US009511082B2

(12) United States Patent
Weers

(10) Patent No.: US 9,511,082 B2
(45) Date of Patent: *Dec. 6, 2016

(54) LIPID-BASED COMPOSITIONS OF ANTIINFECTIVES FOR TREATING PULMONARY INFECTIONS AND METHODS OF USE THEREOF

(71) Applicant: Insmed Incorporated, Bridgewater, NJ (US)

(72) Inventor: Jeff Weers, Belmont, CA (US)

(73) Assignee: INSMED INCORPORATED, Bridgewater, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/205,918

(22) Filed: Jul. 8, 2016

(65) Prior Publication Data

US 2016/0317563 A1 Nov. 3, 2016

Related U.S. Application Data

(63) Continuation of application No. 14/987,508, filed on Jan. 4, 2016, now Pat. No. 9,402,845, which is a continuation of application No. 14/080,922, filed on Nov. 15, 2013, which is a continuation of application No. 13/666,420, filed on Nov. 1, 2012, now Pat. No. 8,642,075, which is a continuation of application No. 13/527,213, filed on Jun. 19, 2012, now Pat. No. 8,632,804, which is a continuation of application No. 11/634,343, filed on Dec. 5, 2006, now Pat. No. 8,226,975.

(60) Provisional application No. 60/748,468, filed on Dec. 8, 2005.

(51) Int. Cl.

| | | |
|---|---|---|
| A61K 31/496 | (2006.01) | |
| A61K 9/127 | (2006.01) | |
| A61K 9/00 | (2006.01) | |
| A61K 31/7036 | (2006.01) | |
| A61M 15/08 | (2006.01) | |
| A61M 11/00 | (2006.01) | |
| A61M 15/00 | (2006.01) | |
| A61M 11/02 | (2006.01) | |

(52) U.S. Cl.
CPC ......... *A61K 31/7036* (2013.01); *A61K 9/0073* (2013.01); *A61K 9/127* (2013.01); *A61M 11/001* (2014.02); *A61M 11/005* (2013.01); *A61M 11/006* (2014.02); *A61M 11/02* (2013.01); *A61M 15/009* (2013.01); *A61M 15/0091* (2013.01); *A61M 15/08* (2013.01)

(58) Field of Classification Search
CPC ........................... A61K 31/496; A61K 9/0073
See application file for complete search history.

(56) References Cited

U.S. PATENT DOCUMENTS

| | | |
|---|---|---|
| 3,091,572 A | 5/1963 | Luedemann et al. |
| 3,136,704 A | 6/1964 | Charney |
| 4,235,871 A | 11/1980 | Papahadjopoulos et al. |
| 4,372,949 A | 2/1983 | Kodama et al. |
| 4,394,448 A | 7/1983 | Szoka, Jr. et al. |
| 4,396,630 A | 8/1983 | Riedl et al. |
| 4,451,447 A | 5/1984 | Kaplan et al. |
| 4,515,736 A | 5/1985 | Deamer |
| 4,522,803 A | 6/1985 | Lenk et al. |
| 4,547,490 A | 10/1985 | Ecanow et al. |
| 4,588,578 A | 5/1986 | Fountain et al. |
| 4,606,939 A | 8/1986 | Frank et al. |
| 4,684,625 A | 8/1987 | Eppstein et al. |
| 4,693,999 A | 9/1987 | Axelsson et al. |
| 4,721,612 A | 1/1988 | Janoff et al. |
| 4,767,874 A | 8/1988 | Shima et al. |
| 4,833,134 A | 5/1989 | Kishimoto et al. |
| 4,857,311 A | 8/1989 | Domb et al. |
| 4,895,452 A | 1/1990 | Yiournas et al. |
| 4,895,719 A | 1/1990 | Radhakrishnan et al. |
| 4,897,384 A | 1/1990 | Janoff et al. |
| 4,933,121 A | 6/1990 | Law et al. |
| 4,952,405 A * | 8/1990 | Yau-Young ............ A61K 9/127 424/423 |
| 4,963,367 A | 10/1990 | Ecanow |

(Continued)

FOREIGN PATENT DOCUMENTS

| | | |
|---|---|---|
| CA | 2174803 A1 | 10/1997 |
| CA | 2101241 C | 12/1998 |

(Continued)

OTHER PUBLICATIONS

Webb et al. (Antimicrobial Agents and Chemotherapy, Jan. 1998; 42(1): 45-52).*

Office Action for U.S. Appl. No. 12/598,830, mailed Mar. 7, 2012, 5 pages.

Office Action for U.S. Appl. No. 12/598,830, mailed Oct. 23, 2012, 7 pages.

Office Action for U.S. Appl. No. 12/598,830, mailed Apr. 18, 2014, 5 pages.

(Continued)

*Primary Examiner* — Scott Long
(74) *Attorney, Agent, or Firm* — Cooley LLP

(57) ABSTRACT

A system for treating or providing prophylaxus against a pulmonary infection is disclosed comprising: a) a pharmaceutical formulation comprising a mixture of free antiinfective and antiinfective encapsulated in a lipid-based composition, and b) an inhalation delivery device. A method for providing prophylaxis against a pulmonary infection in a patient and a method of reducing the loss of antiinfective encapsulated in a lipid-based composition upon nebulization comprising administering an aerosolized pharmaceutical formulation comprising a mixture of free antiinfective and antiinfective encapsulated in a lipid-based composition is also disclosed.

30 Claims, 1 Drawing Sheet

(56) References Cited

U.S. PATENT DOCUMENTS

| | | |
|---|---|---|
| 4,975,282 A | 12/1990 | Cullis et al. |
| 4,981,692 A | 1/1991 | Popescu et al. |
| 5,000,958 A | 3/1991 | Fountain et al. |
| 5,006,343 A | 4/1991 | Benson et al. |
| 5,008,050 A | 4/1991 | Cullis et al. |
| 5,023,087 A | 6/1991 | Yau-Young |
| 5,030,453 A | 7/1991 | Lenk et al. |
| 5,041,278 A | 8/1991 | Janoff et al. |
| 5,049,388 A | 9/1991 | Knight et al. |
| 5,049,389 A | 9/1991 | Radhakrishnan |
| 5,059,421 A | 10/1991 | Loughrey et al. |
| 5,059,591 A | 10/1991 | Janoff et al. |
| 5,077,056 A | 12/1991 | Bally et al. |
| 5,169,637 A | 12/1992 | Lenk et al. |
| 5,178,876 A | 1/1993 | Khokhar et al. |
| 5,192,549 A | 3/1993 | Barenolz et al. |
| 5,211,955 A | 5/1993 | Legros et al. |
| 5,252,339 A | 10/1993 | Cristofori et al. |
| 5,264,618 A | 11/1993 | Felgner et al. |
| 5,269,979 A | 12/1993 | Fountain |
| 5,279,833 A | 1/1994 | Rose |
| 5,316,771 A | 5/1994 | Barenholz et al. |
| 5,320,906 A | 6/1994 | Eley et al. |
| 5,334,761 A | 8/1994 | Gebeyehu et al. |
| 5,401,511 A | 3/1995 | Margalit |
| 5,409,704 A | 4/1995 | Bally et al. |
| 5,459,127 A | 10/1995 | Felgner et al. |
| 5,508,269 A | 4/1996 | Smith et al. |
| 5,540,936 A | 7/1996 | Coe et al. |
| 5,543,152 A | 8/1996 | Webb et al. |
| 5,569,464 A | 10/1996 | Endo et al. |
| 5,578,320 A | 11/1996 | Janoff et al. |
| 5,580,575 A | 12/1996 | Unger et al. |
| 5,610,198 A | 3/1997 | Barry, III et al. |
| 5,614,216 A | 3/1997 | Janoff |
| 5,616,334 A | 4/1997 | Janoff et al. |
| 5,631,018 A | 5/1997 | Zalipsky et al. |
| 5,641,662 A | 6/1997 | Debs et al. |
| 5,643,599 A | 7/1997 | Lee et al. |
| 5,662,929 A | 9/1997 | Lagace et al. |
| 5,665,383 A | 9/1997 | Grinstaff et al. |
| 5,723,147 A | 3/1998 | Kim et al. |
| 5,736,155 A | 4/1998 | Bally et al. |
| 5,741,516 A | 4/1998 | Webb et al. |
| 5,753,613 A | 5/1998 | Ansell et al. |
| 5,756,120 A | 5/1998 | Hersch et al. |
| 5,756,121 A | 5/1998 | Bracken |
| 5,756,353 A | 5/1998 | Debs |
| 5,759,571 A | 6/1998 | Hersch et al. |
| 5,766,627 A | 6/1998 | Sankaram et al. |
| 5,785,987 A | 7/1998 | Hope et al. |
| 5,795,589 A | 8/1998 | Mayer et al. |
| 5,814,335 A | 9/1998 | Webb et al. |
| 5,820,848 A | 10/1998 | Boni et al. |
| 5,823,178 A | 10/1998 | Lloyd et al. |
| 5,837,279 A | 11/1998 | Janoff et al. |
| 5,837,282 A | 11/1998 | Fenske et al. |
| 5,840,702 A | 11/1998 | Bedwell |
| 5,843,473 A | 12/1998 | Woodle et al. |
| 5,849,490 A | 12/1998 | Schonwetter et al. |
| 5,861,159 A | 1/1999 | Pardoll et al. |
| 5,871,710 A | 2/1999 | Bogdanov et al. |
| 5,875,776 A | 3/1999 | Vaghefi |
| 5,922,350 A | 7/1999 | Janoff et al. |
| 5,939,096 A | 8/1999 | Clerc et al. |
| 5,945,122 A | 8/1999 | Abra et al. |
| 5,958,449 A | 9/1999 | Hersch et al. |
| 5,972,379 A | 10/1999 | Guo et al. |
| 5,993,850 A | 11/1999 | Sankaram et al. |
| 6,045,828 A | 4/2000 | Bystrom et al. |
| 6,051,251 A | 4/2000 | Zalipsky et al. |
| 6,051,549 A | 4/2000 | Roberts et al. |
| 6,086,851 A | 7/2000 | Boni et al. |
| 6,090,407 A | 7/2000 | Knight et al. |
| 6,106,858 A | 8/2000 | Ye et al. |
| 6,124,273 A | 9/2000 | Drohan et al. |
| 6,147,060 A | 11/2000 | Zasloff et al. |
| 6,162,462 A | 12/2000 | Bolotin et al. |
| 6,197,333 B1 | 3/2001 | Onyuksel et al. |
| 6,211,162 B1 | 4/2001 | Dale et al. |
| 6,221,385 B1 | 4/2001 | Camu et al. |
| 6,221,388 B1 | 4/2001 | Hersch et al. |
| 6,228,393 B1 | 5/2001 | DiCosmo et al. |
| 6,274,175 B1 | 8/2001 | Gombotz et al. |
| 6,316,024 B1 | 11/2001 | Allen et al. |
| 6,338,859 B1 | 1/2002 | Leroux et al. |
| 6,348,069 B1 | 2/2002 | Vacanti et al. |
| 6,352,996 B1 | 3/2002 | Cao et al. |
| 6,355,267 B1 | 3/2002 | Collins |
| 6,387,886 B1 | 5/2002 | Montgomery et al. |
| 6,419,901 B2 | 7/2002 | Placke et al. |
| 6,440,393 B1 | 8/2002 | Waldrep et al. |
| 6,443,898 B1 | 9/2002 | Unger et al. |
| 6,447,753 B2 | 9/2002 | Edwards et al. |
| 6,451,784 B1 | 9/2002 | Placke et al. |
| 6,458,373 B1 | 10/2002 | Lambert et al. |
| 6,468,532 B1 | 10/2002 | Hsei et al. |
| 6,475,779 B2 | 11/2002 | Mathiowitz et al. |
| 6,492,560 B2 | 12/2002 | Wilbur et al. |
| 6,497,901 B1 | 12/2002 | Royer |
| 6,509,323 B1 | 1/2003 | Davis et al. |
| 6,511,676 B1 | 1/2003 | Boulikas |
| 6,521,211 B1 | 2/2003 | Unger et al. |
| 6,521,736 B2 | 2/2003 | Watterson et al. |
| 6,534,018 B1 | 3/2003 | Baker et al. |
| 6,596,305 B1 | 7/2003 | Edgerly-Plug |
| 6,599,912 B1 | 7/2003 | Au et al. |
| 6,613,352 B2 | 9/2003 | Lagace et al. |
| 6,615,824 B2 | 9/2003 | Power |
| 6,623,671 B2 | 9/2003 | Coe et al. |
| 6,759,057 B1 | 7/2004 | Weiner et al. |
| 6,770,291 B2 | 8/2004 | Smyth-Templeton et al. |
| 6,843,942 B2 | 1/2005 | Katinger et al. |
| 6,855,296 B1 | 2/2005 | Baker et al. |
| 6,890,555 B1 | 5/2005 | Desai et al. |
| 6,900,184 B2 | 5/2005 | Cohen et al. |
| 6,916,490 B1 | 7/2005 | Garver et al. |
| 6,948,491 B2 | 9/2005 | Loeffler et al. |
| 6,962,151 B1 | 11/2005 | Knoch et al. |
| 6,991,809 B2 | 1/2006 | Anderson |
| 7,063,860 B2 | 6/2006 | Chancellor et al. |
| 7,100,600 B2 | 9/2006 | Loeffler et al. |
| 7,244,413 B2 | 7/2007 | Barbera-Guillem |
| 7,331,339 B2 | 2/2008 | Smith et al. |
| 7,368,102 B2 | 5/2008 | Tarara et al. |
| 7,544,369 B2 | 6/2009 | Boni et al. |
| 7,600,511 B2 | 10/2009 | Power et al. |
| 7,718,189 B2 | 5/2010 | Boni et al. |
| 7,748,377 B2 | 7/2010 | Smith et al. |
| 7,879,351 B2 | 2/2011 | Li et al. |
| 7,971,588 B2 | 7/2011 | Fink et al. |
| 8,071,127 B2 | 12/2011 | Cipolla et al. |
| 8,100,162 B2 | 1/2012 | Joern et al. |
| 8,119,156 B2 | 2/2012 | Cipolla et al. |
| 8,226,975 B2 | 7/2012 | Weers |
| 8,268,347 B1 | 9/2012 | Cipolla et al. |
| 8,414,915 B2 | 4/2013 | Cipolla et al. |
| 8,632,804 B2 | 1/2014 | Weers |
| 8,642,075 B2 | 2/2014 | Weers |
| 8,673,348 B2 | 3/2014 | Weers |
| 8,673,349 B2 | 3/2014 | Weers |
| 8,679,532 B2 | 3/2014 | Weers |
| 8,802,137 B2 | 8/2014 | Boni et al. |
| 9,028,864 B2 | 5/2015 | Cipolla et al. |
| 9,078,897 B1 | 7/2015 | Cipolla et al. |
| 9,114,081 B2 | 8/2015 | Gupta |
| 9,119,783 B2 | 9/2015 | Gupta |
| 9,259,424 B2 | 2/2016 | Cipolla et al. |
| 9,333,214 B2 | 5/2016 | Gupta |
| 9,402,845 B2 * | 8/2016 | Weers ................. A61K 9/0073 |
| 2001/0006660 A1 | 7/2001 | Legace et al. |
| 2002/0035061 A1 | 3/2002 | Krieger et al. |
| 2002/0052390 A1 | 5/2002 | Ponikau |
| 2002/0086852 A1 | 7/2002 | Cantor et al. |

(56) References Cited

U.S. PATENT DOCUMENTS

| | | |
|---|---|---|
| 2002/0187105 A1 | 12/2002 | Zou et al. |
| 2003/0059375 A1 | 3/2003 | Perez-Soler et al. |
| 2003/0099697 A1 | 5/2003 | Panzner et al. |
| 2003/0118636 A1 | 6/2003 | Friesen et al. |
| 2003/0138481 A1 | 7/2003 | Zadi |
| 2003/0224039 A1 | 12/2003 | Boni et al. |
| 2004/0009126 A1* | 1/2004 | Pilkiewicz ........... A61K 9/0019 424/46 |
| 2004/0032037 A1 | 2/2004 | Katinger et al. |
| 2004/0091541 A1 | 5/2004 | Unger |
| 2004/0101553 A1 | 5/2004 | Lee et al. |
| 2004/0142025 A1 | 7/2004 | MacLachlan et al. |
| 2004/0142026 A1 | 7/2004 | Boni et al. |
| 2004/0180082 A1 | 9/2004 | Kang et al. |
| 2005/0019926 A1 | 1/2005 | Gonda et al. |
| 2005/0025822 A1 | 2/2005 | Wong et al. |
| 2005/0042341 A1 | 2/2005 | Thomas et al. |
| 2005/0113337 A1 | 5/2005 | Taneja et al. |
| 2005/0214224 A1 | 9/2005 | Weers et al. |
| 2005/0220752 A1 | 10/2005 | Charmot et al. |
| 2005/0249795 A1 | 11/2005 | Zhang et al. |
| 2006/0062738 A1 | 3/2006 | Hofmann et al. |
| 2006/0067998 A1 | 3/2006 | Kurzrock et al. |
| 2006/0073198 A1 | 4/2006 | Boni et al. |
| 2006/0110441 A1 | 5/2006 | Wong et al. |
| 2006/0217603 A1 | 9/2006 | Nagai et al. |
| 2007/0077290 A1 | 4/2007 | Li et al. |
| 2007/0081963 A1 | 4/2007 | Oh et al. |
| 2007/0196461 A1 | 8/2007 | Weers |
| 2007/0267010 A1 | 11/2007 | Fink et al. |
| 2008/0089927 A1 | 4/2008 | Malinin |
| 2008/0131497 A1 | 6/2008 | Perkins et al. |
| 2008/0246472 A1 | 10/2008 | Igney et al. |
| 2009/0104256 A1 | 4/2009 | Gupta |
| 2009/0269396 A1 | 10/2009 | Cipolla et al. |
| 2009/0274754 A1 | 11/2009 | Cipolla et al. |
| 2010/0068257 A1 | 3/2010 | Boni et al. |
| 2010/0196455 A1 | 8/2010 | Malinin |
| 2010/0260829 A1 | 10/2010 | Boni et al. |
| 2011/0064796 A1 | 3/2011 | Cipolla et al. |
| 2011/0150983 A1 | 6/2011 | Cipolla et al. |
| 2011/0159079 A1 | 6/2011 | Li et al. |
| 2012/0010162 A1 | 1/2012 | Norling |
| 2012/0244206 A1 | 9/2012 | Cipolla et al. |
| 2013/0028960 A1 | 1/2013 | Weers |
| 2013/0052260 A1 | 2/2013 | Weers |
| 2013/0064883 A1 | 3/2013 | Weers |
| 2013/0071468 A1 | 3/2013 | Weers |
| 2013/0071469 A1 | 3/2013 | Weers |
| 2013/0087480 A1 | 4/2013 | Stark et al. |
| 2013/0089598 A1 | 4/2013 | Gupta |
| 2013/0121918 A1 | 5/2013 | Hong et al. |
| 2013/0136788 A1 | 5/2013 | Gupta |
| 2013/0330400 A1 | 12/2013 | Perkins et al. |
| 2013/0330440 A1 | 12/2013 | Fulgham |
| 2014/0072620 A1 | 3/2014 | Weers |
| 2014/0248335 A1 | 9/2014 | Malinin |
| 2014/0314835 A1 | 10/2014 | Boni et al. |
| 2015/0110855 A1 | 4/2015 | Cipolla et al. |
| 2015/0272880 A1 | 10/2015 | Seidel et al. |
| 2015/0283076 A1 | 10/2015 | Cipolla et al. |
| 2015/0283133 A1 | 10/2015 | Gonda et al. |
| 2016/0120806 A1 | 5/2016 | Cipolla et al. |
| 2016/0143849 A1 | 5/2016 | Gupta |
| 2016/0151402 A1 | 6/2016 | Gupta |
| 2016/0184301 A1* | 6/2016 | Weers .................. A61K 9/0073 424/450 |
| 2016/0184302 A1* | 6/2016 | Weers .................. A61K 9/0073 424/450 |

FOREIGN PATENT DOCUMENTS

| | | |
|---|---|---|
| CA | 2215716 C | 12/1999 |
| CN | 1747738 | 3/2006 |
| EP | 0069307 | 1/1983 |
| EP | 0274431 | 5/1994 |
| EP | 0652008 | 5/1995 |
| EP | 1083881 | 3/2001 |
| EP | 1083886 | 3/2001 |
| EP | 1190705 | 3/2002 |
| EP | 0825852 | 7/2004 |
| EP | 2457609 | 5/2012 |
| GB | 2145107 | 3/1985 |
| JP | S63-500175 | 1/1988 |
| JP | S63-239213 | 10/1988 |
| JP | H10-511363 | 11/1998 |
| JP | 2006-028069 | 2/2006 |
| UA | 27298 | 10/2007 |
| UA | 27804 | 11/2007 |
| WO | WO 85/00968 | 3/1985 |
| WO | WO 86/06959 | 12/1986 |
| WO | WO 87/00043 | 1/1987 |
| WO | WO 87/02219 | 4/1987 |
| WO | WO 88/04573 | 6/1988 |
| WO | WO 91/09616 | 7/1991 |
| WO | WO 91/16882 | 11/1991 |
| WO | WO 93/12240 | 6/1993 |
| WO | WO 94/12155 | 6/1994 |
| WO | WO 94/12156 | 6/1994 |
| WO | WO 94/22430 | 10/1994 |
| WO | WO 96/08235 | 3/1996 |
| WO | WO 96/19199 | 6/1996 |
| WO | WO 96/19972 | 7/1996 |
| WO | WO 97/29851 | 8/1997 |
| WO | WO 99/30686 | 6/1999 |
| WO | WO 99/51202 | 10/1999 |
| WO | WO 99/61003 | 12/1999 |
| WO | WO 99/65466 | 12/1999 |
| WO | WO 00/27359 | 5/2000 |
| WO | WO 00/29103 | 5/2000 |
| WO | WO 00/45791 | 8/2000 |
| WO | WO 01/00173 | 1/2001 |
| WO | WO 01/05373 | 1/2001 |
| WO | WO 01/15678 | 3/2001 |
| WO | WO 01/18280 | 3/2001 |
| WO | WO 01/32246 | 5/2001 |
| WO | WO 02/32400 | 4/2002 |
| WO | WO 02/43699 | 6/2002 |
| WO | WO 03/045965 | 6/2003 |
| WO | WO 03/075889 | 9/2003 |
| WO | WO 03/075890 | 9/2003 |
| WO | WO 2004/002453 | 1/2004 |
| WO | WO 2004/047802 | 6/2004 |
| WO | WO 2004/054499 | 7/2004 |
| WO | WO 2004/110346 | 12/2004 |
| WO | WO 2004/110493 | 12/2004 |
| WO | WO 2006/108556 | 10/2006 |
| WO | WO 2007/011940 | 1/2007 |
| WO | WO 2007/012191 | 2/2007 |
| WO | WO 2007/067520 | 6/2007 |
| WO | WO 2007/117509 | 10/2007 |
| WO | WO 2007/117550 | 10/2007 |
| WO | WO 2008/039989 | 4/2008 |
| WO | WO 2008/137717 | 11/2008 |
| WO | WO 2008/137917 | 11/2008 |
| WO | WO 2010/045209 | 4/2010 |
| WO | WO 2010/111641 | 9/2010 |
| WO | WO 2011/050206 | 4/2011 |
| WO | WO 2012/050945 | 4/2012 |
| WO | WO 2013/177226 | 11/2013 |
| WO | WO 2014/052634 | 4/2014 |
| WO | WO 2015/017807 | 2/2015 |

OTHER PUBLICATIONS

Office Action for U.S. Appl. No. 12/598,830, mailed Nov. 28, 2014, 8 pages.

International Search Report and Written Opinion for International Application No. PCT/US2008/062469, mailed Sep. 18, 2008, 9 pages.

International Preliminary Report on Patentability for International Application No. PCT/US2008/062469, dated Nov. 10, 2009, 7 pages.

(56) References Cited

OTHER PUBLICATIONS

Office Action for U.S. Appl. No. 12/250,412, mailed Dec. 2, 2011, 7 pages.
Office Action for U.S. Appl. No. 12/250,412, mailed Jun. 27, 2011, 6 pages.
Office Action for U.S. Appl. No. 12/250,412, mailed Mar. 24, 2014, 9 pages.
International Search Report and Written Opinion for International Application No. PCT/US2008/062868, mailed Sep. 18, 2008, 7 pages.
International Preliminary Report on Patentability for International Application No. PCT/US2008/062868, dated Nov. 10, 2009, 5 pages.
Examination Report for Australian Patent Application No. 2009303542, dated Jun. 20, 2012, 3 pages.
Office Action for Chilean Application No. 814-2011, dated Apr. 8, 2014, 6 pages.
Office Action for Chilean Application No. 814-2011, dated Nov. 4, 2014, 5 pages.
Office Action for Chinese Patent Application No. 200980140740.2, dated Jul. 3, 2012, 2 pages.
Office Action for Chinese Patent Application No. 200980140740.2, dated Jun. 4, 2013, 7 pages.
Office Action for Chinese Application No. 200980140740.2, dated Mar. 5, 2014, 5 pages.
Office Action for Indonesian Application No. W00201101412, dated Feb. 28, 2014, 1 page.
Office Action for Israel Application No. 212268, dated Dec. 9, 2013, 2 pages.
Office Action for Japanese Application No. 2011-532180, dated May 1, 2014, 7 pages.
Office Action for Japanese Application No. 2011-532180, dated Jan. 23, 2014, 4 pages.
Office Action for New Zealand Patent Application No. 592217, mailed Sep. 1, 2011, 2 pages.
Office Action for New Zealand Patent Application No. 592217, mailed Feb. 5, 2013, 2 pages.
Office Action for Philippine Application No. 12011500726, mailed Apr. 24, 2014, 1 page.
Office Action for Russian Application No. 2011119018, dated Mar. 5, 2014, 3 pages.
Search Report and Written Opinion for Singapore Application No. 201102419-7, mailed Sep. 7, 2012, 12 pages.
Second Written Opinion for Singapore Application No. 201102419-7, mailed Sep. 4, 2014, 13 pages.
Office Action for Ukraine Application No. 201105955, dated Jun. 7, 2013, 2 pages.
Written Opinion for International Application No. PCT/US2009/060468, mailed Jun. 24, 2010, 3 pages.
International Preliminary Report on Patentability for International Application No. PCT/US2009/060468, dated Apr. 19, 2011, 4 pages.
Office Action for Japanese Application No. 2014-075240, dated Mar. 9, 2015, 2 pages.
First Examination Report for New Zealand Patent Application No. 606383, dated Feb. 5, 2013, 2 pages.
Office Action for U.S. Appl. No. 13/480,246, mailed Jan. 10, 2013, 7 pages.
Office Action for U.S. Appl. No. 13/480,246, mailed Apr. 10, 2014, 7 pages.
Office Action for Australian Patent Application No. 2003304204, mailed Jun. 25, 2008, 3 pages.
Office Action for Canadian Patent Application No. 2504317, dated Jan. 27, 2011, 2 pages.
Office Action for Canadian Patent Application No. 2504317, dated Jun. 16, 2010, 3 pages.
First Office Action for Chinese Patent Application No. 200380106534.2, dated Aug. 11, 2006, 3 pages.
Second Office Action for Chinese Patent Application No. 200380106534.2 [no date], 4 pages.
Third Office Action for Chinese Patent Application No. 200380106534.2, dated May 22, 2009, 4 pages.
Supplementary European Search Report for European Application No. 03816990.0, mailed Jan. 12, 2009, 5 pages.
Summons to Attend Oral Hearing for European Application No. 03816990.0, mailed Dec. 21, 2011, 7 pages.
Office Action for European Application No. 03816990.0, mailed Jun. 17, 2011, 5 pages.
Office Action for European Application No. 03816990.0, mailed Apr. 24, 2009, 6 pages.
Office Action for European Application No. 03816990.0, mailed Jun. 5, 2012, 3 pages.
Office Action for Israel Application No. 168279, dated Aug. 25, 2014, 2 pages.
Office Action for Israel Application No. 168279, dated Mar. 19, 2014, 2 pages.
Office Action for Israel Patent Application No. 168279, dated Nov. 3, 2010, 1 page.
Office Action for Israel Patent Application No. 168279, dated Aug. 17, 2009, 2 pages.
Office Action for Israel Patent Application No. 168279, dated Jun. 23, 2008, 1 page.
Office Action for Israel Application No. 168279, dated Jun. 6, 2012, 1 page.
Office Action for Indian Patent Application No. 2219/DELNP/2005, dated Jan. 3, 2007, 2 pages.
Decision of Refusal for Japanese Patent Application No. 2005-500829, dated Feb. 14, 2012, 2 pages.
Notification of Reasons for Refusal for Japanese Patent Application No. 2005-500829, dated Feb. 15, 2011, 3 pages.
Notification of Reasons for Refusal for Japanese Patent Application No. 2005-500829, dated Jul. 6, 2010, 3 pages.
Office Action for Korean Patent Application No. 10-2005-7007679, dated Dec. 26, 2011, 10 pages.
Office Action for Korean Patent Application No. 10-2005-7007679, dated Jan. 18, 2011, 13 pages.
Office Action for Korean Patent Application No. 10-2005-7007679, dated Dec. 26, 2012, 3 pages.
Office Action for Mexican Patent Application No. PA/a/2005/004580, mailed Aug. 25, 2009, 3 pages.
Third Office Action for Mexican Patent Application No. PA/a/2005/004580, mailed Dec. 10, 2008, 3 pages.
Second Office Action for Mexican Patent Application No. PA/a/2005/004580, mailed May 9, 2008, 2 pages.
First Office Action for Mexican Patent Application No. PA/a/2005/004580, mailed Jan. 30, 2008, 2 pages.
Office Action for New Zealand Patent Application No. 540087, dated Jan. 4, 2008, 2 pages.
Office Action for New Zealand Patent Application No. 540087, dated Sep. 14, 2006, 2 pages.
Office Action for U.S. Appl. No. 10/696,389, mailed Nov. 14, 2008, 6 pages.
Office Action for U.S. Appl. No. 10/696,389, mailed Mar. 28, 2008, 11 pages.
Office Action for U.S. Appl. No. 10/696,389, mailed Oct. 10, 2007, 10 pages.
Office Action for U.S. Appl. No. 10/696,389, mailed Apr. 2, 2007, 9 pages.
International Search Report for International Application No. PCT/US2003/034240, mailed Jul. 12, 2005, 1 page.
International Preliminary Report on Patentability for International Application No. PCT/US2003/034240, mailed May 6, 2013, 5 pages.
Office Action for Japanese Patent Application No. 2011-001318, mailed Feb. 12, 2013, 3 pages.
Official Action for Korean Application No. 10-2013-7010499, dated Sep. 2, 2013, 4 pages.
Office Action for Mexican Patent Application No. MX/a/2010/000195, mailed Feb. 1, 2012, 2 pages.
Office Action for Mexican Patent Application No. MX/a/2010/000195, mailed Jul. 27, 2011, 2 pages.
Office Action for Mexican Patent Application No. MX/a/2010/000195, mailed Oct. 2, 2012, 3 pages.

(56) References Cited

OTHER PUBLICATIONS

Office Action for Mexican Patent Application No. MX/a/2010/000195, mailed May 31, 2013, 2 pages.
Office Action for New Zealand Patent Application No. 564543, mailed Jan. 4, 2008, 2 pages.
Examiner's First Report for Australian Patent Application No. 2006270008, dated Dec. 10, 2010, 3 pages.
Office Action for Canadian Patent Application No. 2,614,764, dated Nov. 14, 2012, 4 pages.
First Office Action for Chinese Patent Application No. 200680034397.X, dated Jan. 22, 2010, 24 pages.
Second Office Action for Chinese Patent Application No. 200680034397.X, dated Feb. 9, 2011, 21 pages.
Third Office Action for Chinese Patent Application No. 200680034397.X, dated Mar. 12, 2012, 5 pages.
Fourth Office Action for Chinese Patent Application No. 200680034397.X, dated Dec. 4, 2012, 3 pages.
Office Action for Columbian Patent Application No. 08016117, dated Jun. 26, 2012, 8 pages.
Office Action for Columbian Patent Application No. 08016117, dated Jan. 14, 2013, 11 pages.
Office Action for Costa Rican Patent Application No. 9736, dated Apr. 22, 2013, 7 pages.
Office Action for Egyptian Patent Application No, PCT 84/2008, mailed Oct. 24, 2012, 3 pages.
Supplementary European Search Report for European Application No. 06787716.7, mailed Dec. 29, 2011, 7 pages.
Office Action for European Application No. 06787716.7, dated Oct. 26, 2012, 3 pages.
Generics [UK] Ltd.'s Notice of Opposition for European Application No. 06787716.7, filed Jun. 4, 2014, 17 pages.
Patentee's Response to Notice of Opposition and Declaration of Lee Leserman for European Application No. 06787716.7, filed Jan. 16, 2015, 58 pages.
Office Action for Israel Application No. 188406, dated Aug. 25, 2014, 2 pages.
Office Action for Israel Patent Application No. 188406, dated Jun. 13, 2011, 4 pages.
Office Action for Israel Patent Application No. 188406, dated Apr. 26, 2010, 1 page.
Office Action for Israel Patent Application No. 188406, dated Jan. 6, 2013, 1 page.
Office Action for Indian Application No. 353/DELNP/2008, dated Jul. 26, 2013, 2 pages.
Office Action for Japanese Patent Application No. 2008-522895, dated Apr. 17, 2012, 4 pages.
Office Action for Japanese Application No. 2008-522895, dated Aug. 27, 2013, 5 pages.
Office Action for Korean Patent Application No. 10-2008-7002031, dated Dec. 21, 2012, 7 pages.
Office Action for Mexican Patent Application No. MX/a/2008/000425, dated Jun. 2, 2010, 2 pages.
Office Action for New Zealand Patent Application No. 565300, dated Feb. 24, 2011, 2 pages.
Office Action for New Zealand Patent Application No. 565300, dated Nov. 11, 2009, 2 pages.
Office Action for New Zealand Patent Application No. 565300, dated May 31, 2011, 2 pages.
Office Action for U.S. Appl. No. 11/185,448, mailed Dec. 17, 2009, 11 pages.
Office Action for U.S. Appl. No. 11/185,448, mailed Jun. 30, 2009, 10 pages.
International Search Report and Written Opinion for International Application No. PCT/US2006/027859, mailed Aug. 14, 2007, 8 pages.
International Preliminary Report on Patentability for International Application No. PCT/US2006/027859, dated Jan. 22, 2008, 6 pages.
Office Action for Canadian Patent Application No. 2,646,255, dated Feb. 4, 2013, 5 pages.
Office Action for Chinese Application No. 201310149581.0, mailed Apr. 21, 2014, 6 pages.
Office Action for Chinese Application No. 201310149581.0, mailed Oct. 17, 2014, 7 pages.
Supplementary European Search Report for European Application No. 07754853, mailed Jan. 16, 2013, 8 pages.
Office Action for European Application No. 07754853.5, mailed Feb. 3, 2014, 4 pages.
Office Action for Israel Application No. 216401, dated May 27, 2014, 2 pages.
Office Action for Japanese Patent Application No. 2009-504281, dated Sep. 4, 2012, 2 pages.
Office Action for Japanese Application No. 2009-504281, mailed Nov. 1, 2013, 5 pages.
Office Action for Korean Application No. 10-2013-7031379, dated Feb. 25, 2014, 3 pages.
Office Action for Mexican Patent Application No. MX/a/2008/012684, dated Jul. 8, 2011, 2 pages.
Office Action for Mexican Patent Application No. MX/a/2008/012684, dated Apr. 5, 2011, 2 pages.
Office Action for U.S. Appl. No. 11/398,859, mailed Jun. 4, 2010, 7 pages.
Office Action for U.S. Appl. No. 11/398,859, mailed Sep. 11, 2009, 12 pages.
International Search Report and Written Opinion for International Application No. PCT/US2007/008404, mailed Sep. 26, 2008, 6 pages.
International Preliminary Report on Patentability for International Application No. PCT/US2007/008404, dated Oct. 21, 2008, 4 pages.
Office Action for Canadian Application No. 2,838,108, mailed Jan. 6, 2015, 3 pages.
European Search Report for European Patent Application No. 11159754.8, mailed Jun. 22, 2011, 5 pages.
Office Action for Japanese Application No. 2013-146934, mailed May 26, 2014, 6 pages.
Office Action for Korean Application No. 10-2014-7005780, Jun. 26, 2014, 4 pages.
Office Action for U.S. Appl. No. 12/424,177, mailed Jul. 21, 2014, 10 pages.
Office Action for U.S. Appl. No. 12/424,177, mailed Mar. 16, 2012, 15 pages.
Office Action for U.S. Appl. No. 12/424,177, mailed Aug. 31, 2011, 10 pages.
Office Action for U.S. Appl. No. 12/424,177, mailed Dec. 24, 2013, 10 pages.
Office Action for Canadian Application No. 2,853,611, mailed Jul. 9, 2014, 3 pages.
Office Action for Canadian Application No. 2,853,611, mailed Mar. 5, 2015, 3 pages.
European Search Report for European Patent Application No. 13175824.5, mailed Sep. 16, 2013, 8 pages.
Office Action for Japanese Application No. 2013-167610, dated Aug. 8, 2014, 4 pages.
Office Action for U.S. Appl. No. 12/748,756, mailed Jan. 27, 2012, 9 pages.
Office Action for U.S. Appl. No. 12/748,756, mailed Aug. 23, 2012, 8 pages.
Office Action for Japanese Application No. 2014-040222, dated Feb. 10, 2015, 1 page.
Office Action for U.S. Appl. No. 12/983,659, mailed Dec. 2, 2013, 14 pages.
Office Action for U.S. Appl. No. 12/983,659, mailed Jun. 17, 2014, 11 pages.
European Search Report for European Application No. 14183066.1, mailed Dec. 16, 2014, 11 pages.
Office Action for Australian Patent Application No. 2006322076, mailed Sep. 23, 2011, 2 pages.
Office Action for Canadian Patent Application No. 2,631,872, dated Dec. 7, 2012, 2 pages.
Supplementary European Search Report for European Application No. 06847502.9, mailed Dec. 5, 2012, 7 pages.

(56) References Cited

OTHER PUBLICATIONS

Office Action for European Patent Application No. 06847502.9, mailed Oct. 14, 2013, 6 pages.
Office Action for European Patent Application No. 06847502.9, mailed Jul. 16, 2014, 4 pages.
Office Action for Japanese Patent Application No. 2008-544430, mailed May 26, 2012, 3 pages.
Office Action for U.S. Appl. No. 11/634,343, mailed Jan. 17, 2012, 8 pages.
Office Action for U.S. Appl. No. 11/634,343, mailed Aug. 4, 2011, 17 pages.
Office Action for U.S. Appl. No. 11/634,343, mailed Apr. 5, 2011, 21 pages.
Office Action for U.S. Appl. No. 11/634,343, mailed Sep. 14, 2010, 22 pages.
Office Action for U.S. Appl. No. 11/634,343, mailed Feb. 23, 2010, 16 pages.
Office Action for U.S. Appl. No. 11/634,343, mailed Jun. 19, 2009, 11 pages.
International Search Report and Written Opinion for International Application No. PCT/US2006/046360, mailed Oct. 17, 2007, 5 pages.
International Preliminary Report on Patentability for International Application No. PCT/US2006/046360, dated Jun. 11, 2008, 5 pages.
Office Action for Canadian Application No. 2,838,111, dated Nov. 27, 2014, 4 pages.
Office Action for U.S. Appl. No. 13/527,213, mailed Mar. 11, 2013, 12 pages.
Office Action for U.S. Appl. No. 13/664,181, mailed Feb. 12, 2013, 12 pages.
Office Action for U.S. Appl. No. 13/664,181, mailed Aug. 22, 2013, 9 pages.
Office Action for U.S. Appl. No. 13/666,420, mailed Mar. 5, 2013, 10 pages.
Office Action for U.S. Appl. No. 13/675,559, mailed Mar. 19, 2013, 13 pages.
Office Action for U.S. Appl. No. 13/675,559, mailed Aug. 20, 2013, 9 pages.
Office Action for U.S. Appl. No. 13/675,587, mailed Apr. 4, 2013, 11 pages.
Office Action for U.S. Appl. No. 13/675,587, mailed Aug. 21, 2013, 9 pages.
Office Action for U.S. Appl. No. 14/080,922, mailed Jun. 12, 2014, 11 pages.
Office Action for U.S. Appl. No. 14/080,922, mailed Sep. 18, 2014, 10 pages.
Office Action for U.S. Appl. No. 14/080,922, mailed Mar. 3, 2015, 16 pages.
Office Action for U.S. Appl. No. 14/080,922, mailed Aug. 10, 2015, 17 pages.
Supplementary European Search Report and Written Opinion for European Application No. 07754936.8, mailed Jan. 18, 2013, 9 pages.
Office Action for European Application No. 07754936.8, mailed Sep. 2, 2014, 7 pages.
Office Action for Japanese Patent Application No. 2009-504301, dated Sep. 4, 2012, 4 pages.
Office Action for Japanese Patent Application No. 2009-504301, mailed Oct. 31, 2013, 5 pages.
Office Action for U.S. Appl. No. 11/696,343, mailed Oct. 21, 2011, 16 pages.
Office Action for U.S. Appl. No. 11/696,343, mailed May 10, 2011, 11 pages.
Office Action for U.S. Appl. No. 11/696,343, mailed May 23, 2014, 18 pages.
Office Action for U.S. Appl. No. 11/696,343, mailed Feb. 3, 2015, 11 pages.
International Search Report and Written Opinion for International Application No. PCT/US2007/008500, mailed Sep. 26, 2008, 9 pages.
International Preliminary Report on Patentability for International Application No. PCT/US2007/008500, dated Oct. 21, 2008, 8 pages.
International Search Report and Written Opinion for International Application No. PCT/US2013/042113, mailed Sep. 4, 2013, 13 pages.
International Preliminary Report on Patentability for International Application No. PCT/US2013/042113, dated Nov. 25, 2014, 9 pages.
Allen, T. M. et al., "Effect of liposome size and drug release properties of pharmacokinetics of encapsulated drug to rats," The Journal of Pharmacology and Experimental Therapeutics, 226(2):539-544 (1983).
Alton et al., "Cationic lipid-mediated CFTR gene transfer to the lungs and nose of patients with cystic fibrosis: a double-blind placebo-controlled trial," The Lancet, 353(9157):947-954 (1999).
Andrews, J. M., "Determination of minimum inhibitory concentrations," Journal of Antimicrobial Chemotherapy, 48(S1):5-14 (2001).
Antos, M. et al., "Antibacterial activity of liposomal amikacin against Pseudomonas aeruginosa in vitro," Pharmacological Research, 32(1/2):84-87 (1995).
Bakker-Woudenberg, I. et al., "Efficacy of gentamicin or ceftazidine entrapped in liposomes with prolonged blood circulation and enhanced localization in Klebsiella pneumoniae-infected lung tissue," The Journal Infectious Diseases, 171:938-947 (1995).
Bakker-Woudenberg, I. A. J. M. et al., "Long-Circulating Sterically Stabilized Liposomes in the Treatment of Infections," Method in Enzymology, Available online Feb. 21, 2005, 391:228-260 (2005).
Ball, V. et al., "Complexation mechanism of bovine serum albumin and poly(allylamine hydrochloride)," J. Phys. Chem. B., 106(9):2357-2364 (2002).
Bangham, A. D. et al., "Diffusion of univalent ions across the lamellae of swollen phospholipids," J. Mol. Biol., 13(1):238-252 (1965).
Bangham, A. D., Introduction, "Liposomes: An Historical Perspective," in: Liposomes, Ostro, M. J. (ed.), pp. 1-25, Marcel Dekker, Inc., New York (1983).
Bargoni, A. et al., "Transmucosal transport of tobramycin incorporated in solid lipid nanoparticles (SLN) after duodenal administration to rats. Part II—Tissue distribution," Pharmacological Research, 43(5):497-502 (2001).
Beaulac, C. et al., "Eradication of Mucoid Pseudomonas aeruginosa with Fluid Liposome-Encapsulated Tobramycin in an Animal Model of Chronic Pulmonary Infection," Antimicrobial Agents and Chemotherapy, 40(3):665-669 (1996).
Beaulac, C. et al., "In-vitro bactericidal efficacy of sub-MIC concentrations of liposome-encapsulated antibiotic against Gram-negative and Gram-positive bacteria," Journal of Antimicrobial Chemotherapy, 41:35-41 (1998).
Beaulac, C. et al., "Aerolization of low phase transition temperature liposomal tobramycin as a dry powder in an animal model of chronic pulmonary infection caused by Pseudomonas aeruginosa," Journal Drug Targeting, 7(1):33-41 (1999).
Beaulac, C. et al., "In vitro kinetics of drug release and pulmonary retention of microencapsulated antibiotic in liposomal formulations in relation to the lipid composition," Journal Microencapsulation 14(3):335-348 (1997).
Bermudez, L. E. et al., "Treatment of disseminated mycobacterium avium complex infection of beige mice with liposome-encapsulated aminoglycosides," The Journal of Infectious Diseases, 161(6):1262-1268 (1990).
Bilodeau, M. et al., "Kanamycin aerosol therapy in 200 cases of bronchopulmonary suppurations," Can. Med. Assoc. J., 89:537-541 (1963) (with English Abstract).
Blaser, J. et al., "Once daily dosing of aminoglycosides," Eur. Clin. Microbiol. Infect. Dis., 14(12):1029-1038 (1995).
Bucke, W. E. et al., "Surface-modified amikacin-liposomes: organ distribution and interaction with plasma proteins," Journal of Drug Targeting, 5(2):99-108 (1997).

(56) References Cited

OTHER PUBLICATIONS

Bunderberg de Jong, H. G. et al., Koazevation (Entmischung in Kolloidalen Systemen), Koll, Zeitsch, 50(10):39-48 (1930).

Carlier, M. B. et al., "Inhibition of lysosomal phospholipases by aminoglycoside antibiotics: in vitro comparative studies," Antimicrobial Agents and Chemotherapy, 23(3):440-449 (1983).

Cantin, A. M. et al., "Aerosolized prolastin suppresses bacterial proliferation in a model of chronic pseudomonas aeruginosa lung infection," Am. J. Respir. Crit. Care Med., 160:1130-1135 (1999).

Cash, H. A. et al., "A rat model of chronic respiratory infection with Pseudomonas aeruginosa," American Review of Respiratory Disease, 119(3):453-459 (1979).

Challoner, P. B. et al., "Gamma Scintigraphy Lung Deposition Comparison of TOBI in the PARI LC PLUS Nebulizer and the Aerodose Inhaler," American Thoracic Society 97th International Conference, San Francisco, California, Aerogen, Inc. (2001).

Chambless, J. D. et al., "A three-dimensional computer model of four hypothetical mechanisms protecting biofilms from antimicrobials," Appl. Environ. Microbiol., 72(3):2005-2013 (2006).

Chan, C. H. S. et al., "Mycobacteria as a cause of infective exacerbation in bronchiectasis," Postgrad. Med. J., 68:896-899 (1992).

Chapman, D., "Physicochemical Properties of Phospholipids and Lipid-Water Systems," In: Liposome Technology, Chapter 1, vol. I, Preparation of Liposomes, Gregoriadis G. (ed.), CRC Press, Inc., Boca Raton, Florida, pp. 1-18 (1984).

Chmiel, J. F. et al., "State of the art: why do the lungs of patients with cystic fibrosis become infected and why can't they clear the infection?", Respiratory Research, 4:8-20 (2003).

Clancy, J. P. et al., "Phase II studies of nebulised Arikace in CF patients with Pseudomonas aeruginosa infection," Thorax, 68(9):818-825 (2013).

Clay. M. M. et al., "Assessment of jet nebulisers for lung aerosol therapy," Lancet, 2:592-594 (1983).

Colardyn, F., "The efficacy and safety of isepamicin and ceftazidime compared with amikacin and ceftazidime in acute lower respiratory tract infection," Journal of Chemotherapy, 7(2):129-135 (1995).

Coleman, L. T. et al., "Bronchiectasis in children," Journal of Thoracic Imaging, 10(4)268-279 (1995).

Comis, R. L., "Carboplatin in the treatment of non-small cell lung cancer: a review," Oncology, 50(2):37-41 (1993).

Cooksey, R. C. et al., "Antimicrobial susceptibility patterns of Streptococcus pneumoniae," Antimicrobial Agents and Chemotherapy, 13(4):645-648 (1978).

Costerton, J. W. et al., "Bacterial biofilms: A common cause of persistent infections," Science, 284:1318-1322 (1999).

Couvreur, P. et al., "Liposomes and nanoparticles in the treatment of intracellular bacterial infections," Pharmaceutical Research, 8(9):1079-1085 (1991).

Cremades, M. J. et al., "Repeated pulmonary infection by Nocardia asteroides complex in a patient with bronchiectasis," Respiration, 65:211-213 (1998).

Crowther, N. R. et al., "Inhaled aminoglycoside (gentamicin) in bronchiectasis: Dry powder vs. nebulization vs. intravenous therapy," Clinical and Investigative Medicine, Annual Meeting of the Canadian Society for Clinical Investigation, The Royal College of Physicians and Surgeons of Canada and Participating Societies, Toronto, Canada, Abstract 530 (Sep. 24-27, 1998).

Currie, D. C., "Nebulisers for bronchiectasis," Thorax, 52(Suppl. 2):572-574 (1997).

Cynamon, M. H. et al., "Liposome-Encapsulated-Amikacin Therapy of Mycobacterium avium Complex Infection in Geige Mice," Antimicrobial Agents and Chemotherapy, 33(8):1179-1183 (1989).

Dally, M. B. et al., "Ventilatory effects of aerosol gentamicin," Thorax, 33:54-56 (1978).

Damaso, D. et al., "Susceptibility of current clinical isolates of Pseudomonas aeruginosa and enteric gram-negative bacilli to amikacin and other aminoglycoside antibiotics," The Journal of Infectious Diseases, 134:S394-S390 (1976).

Deamer, D. W. et al., "Liposome Preparation: Methods and Mechanisms," Chapter 1 in: Liposomes, Ostro, M. J. (ed.), Marcel Dekker, Inc., New York (1983), 27 pages.

Dees, C. et al., "The mechanism of enhanced intraphagocytic killing of bacteria by liposomes containing antibiotics," Veterinary Immunology and Immunopathology, 24:135-146 (1990).

Del Porto, P. et al., "Dysfunctional CFTR alters the bactericidal activity of human macrophages against Pseudomonas aeruginosa," PLoS One, 6(5):e19970 (2011).

Demaeyer, P. et al., "Disposition of liposomal gentamicin following intrabronchial administration in rabbits," Journal Microencapsulation, 10(1):77-88 (1993).

Deol, P. et al., "Lung specific stealth liposomes: stability, biodistribution and toxicity of liposomal antitubular drugs in mice," Biochimica et Biophysica Acta, 1334:161-172 (1997).

Dequin, P. F. et al., "Urinary excretion reflects lung deposition of aminoglycoside aerosols in cystic fibrosis," Eur. Respir. J., 18(2):316-322 (2001).

Dickie, K. J. et al., "Ventilatory effects of aerosolized kanamycin and polymyxin," Chest, 63(5):694-697 (1973).

Dong, C. et al., "Acacia-gelatin microencapsulated liposomes: preparation, stability and release of acetylsalicylic acid," Pharmaceutical Research, 10(1):141-146 (1993).

Doring, G. et al., "Antibiotic therapy against Pseudomonas aeruginosa in cystic fibrosis: a European consensus," Eur Respir J., 16(4):749-767 (2000).

Drenkard, E. et al., "Pseudomonas biofilm formation and antibiotic resistance are linked to phenotypic variation," Nature, 416:740-743 (2002).

Ehlers, S. et al., "Liposomal amikacin for treatment of M. avium Infections in clinically relevant experimental settings," Zbl. Bakt., 284:218-231 (1996).

El-Din, M. A. T. et al., "Nebulizer therapy with antibiotics in chronic suppurative lung disease," Journal of Aerosol Medicine, 7(4):345-350 (1994).

Eller, J. M. et al., "The therapy of bronchiectasis," Deutsche Medizinische Wochenschrift, 118(44):1608-1610 (1993).

Farber, J. E. et al., "The use of aerosol penicillin and streptomycin in bronchopulmonary infections," California Medicine, 73(3):214-217 (1950).

Fielding, R. M. et al., "Pharmacokinetics and Urinary Excretion of Amikacin in Low-Clearance Unilamellar Liposomes after a Single or Repeated Intravenous Administration in the Rhesus Monkey," Antimicrobial Agents and Chemotherapy, 43(3):503-509 (1999).

Finke, W., "Long-term antibiotic therapy in chronic bronchitis and infectious asthma. Control and prevention of bronchopulmonary disease." Antibiotics and Chemotherapy, 4(3):319-329 (1954).

Fountain, M. W. et al., "Treatment of Brucella canis and Brucella abortus in vitro and in vivo by stable plurilamellar vesicle-encapsulated aminoolycosides," The Journal of Infectious Diseases, 152(3):529-535 (1985).

Garcia, A. T., "Efficacy of amikacin sulfate in lower respiratory infections," Investigacion Medica Internacional, 9(3):235-240 (1982) (with English Abstract).

Geller, D. E. et al., "Pharmacokinetics and bioavailability of aerosolized tobramycin in cystic fibrosis," Chest, 122(1):219-226 (2002).

Gibson, R. L. et al., "Pathophysiology and management of pulmonary infections in cystic fibrosis," American Journal of Respiratory and Critical Care Medicine, 168(8):918-951 (2003).

Gibson, R. L. et al., "Significant microbiological effect of inhaled tobramycin in young children with cystic fibrosis," American Journal of Respiratory and Critical Care Medicine, 167(6):841-849 (2003).

Gilbert, B. E. et al., "Tolerance of volunteers to cyclosporine A-dilauroylphosphatidylcholine liposome aerosol," American Journal of Respiratory and Critical Care Medicine, 156(6):1789-1793 (1997).

Gleiser, C. A. et al., "Pathology of experimental respiratory anthrax in Macaca mulatta," Brit. J. Exp. Path., 44:416-426 (1963).

Goldman, J. M. et al., "Inhaled micronised gentamicin powder: a new delivery system," Thorax, 45:939-940 (1990).

(56) References Cited

OTHER PUBLICATIONS

Gonzales-Rothi, R. J. et al., "Liposomes and pulmonary alveolar macrophages: functional and morphologic interactions," Experimental Lung Research, 17:687-705 (1991).
Goss, C. H. et al., "Update on cystic fibrosis epidemiology," Current Opinion in Pulmonary Medicine, 10(6):510-514 (2004).
Graczyk, J. et al., "Staphylococcal pneumonia—analysis of material of patients treated in lung diseases hospital in years 1981-1994," Pneumonologia I Alergologia Polska, 65(11-12):767-774 (1997).
Greene, K. E. et al., "Radiographic changes in acute exacerbations of cystic fibrosis in adults: A pilot study," AJR, 163:557-562 (1994).
Gunther, A. et al., "Surfactant alteration and replacement in acute respiratory distress syndrome," Respiratory Research, 2(6): 353-364 (2001).
Hagwood, S. et al., "Structure and properties of surfactant protein B," Biochimica et Biophysica Acta., 1408:150-160 (1998).
Hansen, C. R. et al., "Long-term azithromycin treatment of cystic fibrosis patients with chronic pseudomonas aeruginosa infection: an observational cohort study," Journal of Cystic Fibrosis, 4(1):35-40 (2005).
Helbich, T. et al., "High-resolution computed tomography of the lung in young patients with cystic fibrosis," Radiologe, 33(3):142-146 (1993) (English Abstract).
Hess, D. et al., "Medication nebulizer performance. Effects of diluent volume, nebulizer flow, and nebulizer brand," Chest, 110:498-505 (1996).
Hess, D. R., "Nebulizers: Principles and Performance," Respiratory Care, 45(6):609-622 (2000).
Hewitt, W. L. et al., "Antibiotic therapy of abscess of the lung and bronchiectasis," California Medicine, 76(5):319-324 (1952).
Hoffman, L. R. et al., "Aminoglycoside antibiotics induce bacterial biofilm formation," Nature, 436:1171-1175 (2005).
Howell, S. B., "Clinical applications of a novel sustained-release injectable drug delivery system: Depofoam Technology," Cancer Journal, 7:219-227 (2001).
Hrkach, J. S. et al., "Synthesis of poly(L-lactic acid-co-L-lysine) graft copolymers," Macromolecules, 28:4736-4739 (1995).
Hrkach, J. S. et al., "Poly(L-Lactic acid-co-amino acid) graft copolymers: A class of functional biodegradable biomaterials," In: Hydrogels and Biodegradable Polymers for Bioapplications, Chapter 8, ACS Symposium Series No. 627, Ottenbrite, R. M. et al. (eds.), American Chemical Society, pp. 93-102 (1996).
Huang, L. et al., "Progress of liposome's applications in biomedicine," International Journal of Biologicals, 29(3):130-132 and 137 (2006).
Hubble, D., "Discussion on respiratory catarrh in children," Proceedings of the Royal Society of Medicine, 52(9):701-710 (1959).
Hung, O. R. et al., "Pharmacokinetics of inhaled liposome-encapsulated fentanyl," Anesthesiology, 83(2): 277-284 (1995).
Hunt, B. E. et al., "Macromolecular mechanisms of sputum inhibition of tobramycin activity," Antimicrobial Agents and Chemotherapy, 39(1):34-39 (1995).
Ikegami, M. et al., "Surfactant protein metabolism in vivo," Biochimica et Biophysica Acta, 1408:218-225 (1998).
Ikemoto, H. et al., "Susceptibility of bacteria isolated from the patients with lower respiratory tract infections to antibiotics," The Japanese Journal of Antibiotics, 42(11):2350-2353 (1989).
IP, M. S. M. et al., "Bronchiectasis and related disorders," Respirology, 1:107-114 (1996).
Ishii, F. et al., "Procedure for Preparation of Lipid Vesicles (Liposomes) Using the Coacervation (Phase Separation) Technique," Langmuir, 11(2):483-486 (1995).
Janoff, A. S. et al., "Unusual lipid structures selectively reduce the toxicity of amphotericin B," Proc. Nat. Acad. Sci. USA, 85:6122-6126 (1988).
Johansson, J., "Structure and properties of surfactant protein C," Biochimica et Biophysica Acta, 1408:161-172 (1998).
Johnston, M. J. W. et al., "Therapeutically optimized rates of drug release can be achieved by varying the drug-to-lipid ratio in liposomal vincristine formulations," Biochimica et Biophysica Acta, 1758:55-64 (2006).
Katare, O. P. et al., "Enhanced in vivo Performance of LiposomalIndomethacin Derived From Effervescent Granule Based Proliposomes," J. Microencapsulation, 12(5):487-493 (1995).
Kesavalu, L. et al., "Differential effects of free and liposome encapsulated amikacin on the survival of *Mycobacterium avium* complex in mouse peritoneal macrophages," Tubercle, 71:215-218 (1990).
Kim, E. K. et al., "Pharmacokinetics of intravitreally injected liposomes encapsulated tobramycin in normal rabbits," Yonsei Medical Journal, 31(4):308-314 (1990).
Klemens, S. P. et al., "Liposome-encapsulated-gentamicin therapy of *Mycobacterium avium* complex infection in beige mice," Antimicrobial Agents and Chemotherapy, 34(6):967-970 (1990).
Knoch, M. et al., "The customised electronic nebuliser: a new category of liquid aerosol drug delivery systems," Expert Opin. Drug Deliv., 2(2):377-390 (2005).
Knox, K. et al., "Chronic bronchitis. An attempt to control chronic infection with Haemophilus influenzae by aerosol therapy," The Lancet, pp. 120-122 (1955).
Labiris, N. R. et al., "Pulmonary drug delivery. Part II: The role of inhalant delivery devices and drug formulations in Therapeutic effectiveness of aerosolized medications," Br.J.Clin.Pharmacol., 56(6):600-612 (2003).
Lagace, J. et al., "Liposome-encapsulated antibiotics: preparation, drug release and antimicrobial activity against Pseudomona aeruginosa," Journal Microencapsulation, 8(1) 53-61 (1991).
Landyshev, Y. S. et al., "Clinical and experimental aspects of liposomal hydrocortisone treatment of bronchial asthma," Ter. Arkh., 74(8):45-48 (2002).
Lass, J. S. et al., "New advances in aerosolised drug delivery: vibrating membrane nebuliser technology," Expert Opin Drug Deliv., 3(5):693-702 (2006).
Le Brun, P. P. H. et al., "A review of the technical aspects of drug nebulization," Pharmacy World & Science, 22(3):75-81 (2000).
Le Brun, P. P. H. et al., "Inhalation of tobramycin in cystic fibrosis part 1: The choice of a nebulizer," International Journal of Pharmaceutics, 189:205-214 (1999).
Le Brun, P. P. H. et al., "Inhalation of tobramycin in cystic fibrosis part 2: Optimization of the tobramycin solution for a jet and ultrasonic nebulizer," International Journal of Pharmaceutics, 189:215-225 (1999).
Le Brun, P. P. H. et al., "Dry powder inhalation of antibiotics in cystic fibrosis therapy: part 2. Inhalation of a novel colistin dry powder formulation: a feasibility study in healthy volunteers and patients," European Journal of Pharmaceutics and Biopharmaceutics, 54:25-32 (2002).
Li, Z. et al., "Nebulization of liposomal amikacin formulations: SLIT Amikacin," Respiratory Drug Delivery, 3:801-804 (2006).
Li, Z. et al., "Characterization of nebulized liposomal amikacin (Arikace) as a function of droplet size," Journal of Aerosol Medicine and Pulmonary Drug Delivery, 21(3):245-253 (2008).
Lin, H.-C. et al., "Inhaled gentamicin reduces airway neutrophil activity and mucus secretion in bronchiectasis," Am. J. Respir. Crit. Care Med., 155:2024-2029 (1997).
Lutwyche, P. et al., "Intracellular delivery and antibacterial activity of gentamicin encapsulated in pH-sensitive liposomes," Antimicrobial Agents and Chemotherapy, 42(10):2511-2520 (1998).
Majumdar, S. et al., "Efficacies of Liposome-Encapsulated Streptomycin and Ciprofloxacin against *Mycobacterium avium*-M. intracellulare Complex Infections in Human Peripheral Blood Monocyte/Macrophages," Antimicrobial Agents and Chemotherapy, 36(12):2808-2815 (Dec. 1992).
Marcotte, G. V. et al., "Chronic productive cough and bronchiectasis in a 40-year-old woman," Annals of Allergy, Asthma & Immunology, 78(6):559-564 (1997).
Marier, J. F. et al., "Liposomal tobramycin against pulmonary infections of *Pseudomonas aeruginosa*: a pharmacokinetic and

(56) References Cited

OTHER PUBLICATIONS efficacy study following single and multiple intratracheal administrations in rats," Journal Antimicrobial Chemotherapy, 52:247-252 (2003).
Marier, J-F. et al., "Pharmacokinetics and efficacies of liposomal and conventional formulations of tobramycin after intratracheal administration in rats with pulmonary burkholderia cepacia infection," Antimicrobial Agents and Chemotherapy, 46(12):3776-3781 (2002).
Mariotti, A. B. et al., "Aerosol therapy with tobramycin in exacerbations of chronic obstructive lung disease (7 cases)," 66(2):198-202 (1996) (with English Abstract).
Martini, W. Z. et al., "Lung surfactant kinetics in conscious pigs," Am J Physiol., 277(1 Pt 1): E187-E195 (1999).
Marwah, O. S. et al., "Bronchiectasis. How to identify, treat and prevent," Postgrad. Med., 97(2):149-150, 153-156, 159 (1995) (Abstract).
Maurer, N. et al., "Anomalous solubility behavior of the antibiotic ciprofloxacin encapsulated in liposomes: a $^1$H-NMR study," Biochimica et Biophysica Acta, 1374:9-20 (1998).
McAllister, S. M. et al., "Antimicrobial properties of liposomal polymyxin B," Journal of Antimicrobial Chemotherapy, 43:203-210 (1999).
Meers, P. et al., "Biofilm penetration, triggered release and in vivo activity of inhaled liposomal amikacin in chronic Pseudomonas aeruginosa lung infections," Journal of Antimicrobial Chemotherapy, 61(4):859-868 (2008).
Mendelman, P. M. et al., "Aminoglycoside penetration, inactivation, and efficacy in cystic fibrosis sputum," American Review of Respiratory Disease, 132(4):761-765 (1985).
Mohanty, B. et al., "Systematic of alcohol-induced simple coacervation in aqueous gelatin solutions," Biomacromolecules, 4:1080-1086 (2003).
Mombelli, G. et al., "Anti-pseudomonas activity in bronchial secretions of patients receiving amikacin or tobramycin as a continuous infusion," Antimicrobial Agents and Chemotherapy, 19(1):72-75 (1981).
Morgan, J. R. et al., "Preparation and properties of liposome-associated gentamicin," Antimicrobial Agents and Chemotherapy, 17(4):544-548 (1980).
Myers, M. A. et al., "Pulmonary effects of chronic exposure to liposome aerosols in mice," Experimental Lung Research, 19:1-19 (1993).
Nakazawa, S. et al., "Studies on a new aminoglycoside antibiotic, amikacin (BB-K8) in pediatrics," The Japanese Journal of Antibiotics, 27(4):438-445 (1974).
Nasu, M. et al., "Appropriate use of antimicrobial agents," Selection of Anti-infective, Clinic in Japan (Special Number) Infection Disease Study in New Era (first volume), 2003, 61st issue, pp. 718-723.
Newton, D. W. et al., Chapter 4: "Coacervation: Principles and Applications," In: Polymers for Controlled Drug Delivery, Tarcha, P. J. (ed.), CRC Press, Boca Raton, pp. 67-81 (1991).
Nightingale, S. D. et al., "Liposome-encapsulated gentamicin treatment of *Mycobacterium avium-Mycobacterium* intracellulare complex bacteremia in AIDS patients," Antimicrobial Agents and Chemotherapy, 37(9):1869-1872 (1993).
Niven, R. W. et al., "Nebulization of liposomes. I. Effects of lipid composition," Pharmaceutical Research, 7(11):1127-1133 (1990).
Niven, R. W. et al., "Nebulization of liposomes. II. The effects of size and modeling of solute release profiles," Pharmaceutical Research, 8(2):217-221 (1991).
Niven, R. W. et al., "Nebulization of liposomes. III. The effects of operating conditions and local environment," Pharmaceutical Research, 9(4):515-520 (1992).
Oizumi, K. et al., "Therapeutic effect of amikacin for infections with gram-negative bacilli, especially for stubborn respiratory infections," The Japanese Journal of Antibiotics, 31(1):15-23 (1978).
Olsen, A. M., "Streptomycin aerosol in the treatment of chronic bronchiectasis: preliminary report," Staff Meetings of the Mayo Clinic, pp. 53-54 (1946).
Olsen, A. M., "Nebulization therapy in bronchiectasis: The use of penicillin and streptomycin aerosols," In: Collected Papers of The Mayo Clinic and The Mayo Foundation, Hewitt, R. M. et al. (eds.), 38:579-586 (1946).
Olsen, A. M., "Nebulization therapy in bronchiectasis: The use of penicillin and streptomycin aerosols," J.A.M.A., 134(11):947-953 (1947).
Omri, A. et al., "Incorporation, release and in-vitro antibacterial activity of liposomal aminoglycosides against Pseudomonas aeruginosa," Journal Antimicrobial Chemotherapy, 36(4):631-639 (1995).
Omri, A. et al., "Comparison of the bactericidal action of amikacin, netilmicin and tobramtcin in free and liposomal formulation against pseudomonas aeruginosa," Chemotherapy, 42:170-176 (1996).
Omri, A. et al., "Pulmonary retention of free and liposome-encapsulated tobramycin after intratracheal administration in uninfected rats and rats infected with Pseudomonas aeruginosa," Antimicrobial Agents and Chemotherapy, 38(5):1090-1095 (1994).
Pai, V. B. et al., "Efficacy and safety of aerosolized tobramycin in cystic fibrosis," Pediatric Pulmonology, 32(4):314-327 (2001).
Papahadjopoulos, D. et al., "Phospholipid model membranes. I. Structural characteristics of hydrated liquid crystals," Biochimica et Biophysica Acta., 135:624-638 (1967).
Paradisi, F. et al, "Acute and chronic bronchopulmonary infections and aminoglycoside antibiotics," Chemioterapia Antimicrobica, 1(2):224-227 (1978).
Parsek, M. R. et al., "Acyl-homoserine lactone quorum sensing gram-negative bacteria: a signaling mechanism involved in associations with higher organisms," Proc. Nat. Acad. Sci., 97(16):6789-6793 (2000).
Patton, J. S. et al., "The lungs as a portal of entry for systemic drug delivery," Proc. Am. Thor. Soc., 1:338-344 (2004).
Perkins, W. R. et al., "Aerosolization of liposomal amikacin (Arikace) using different nebulizers: Selection of the eflow nebulizer," Poster and Oral Presentation at North American Cystic Fibrosis Conference (Oct. 2007), Pediatric Pulmonology, 42(30):356-357, abs. 434, 12 pages.
Perkins, W. R. et al., "Role of lipid polymorphism in pulmonary surfactant," Science, 273:330-332 (Jul. 1996).
Petersen, E. A. et al., "Liposomal amikacin: improved treatment of *Mycibacterium avium* complex infection in the beige mouse model," Journal Antimicrobial Chemotherapy, 38:819-828 (1996).
Petkowicz, J. et al., "Hypoglycemic Effect of Liposome-Entrapped Insulin Administered by Various Routes into Normal Rats," Pol. J. Pharmacol. Pharm., 41:299-304 (1989).
Pilewski, J. M. et al., "Role of CFTR in airway disease," Physiological Reviews, 79(1):S215-S255 (1999).
Pines, A. et al., "Treatment of severe pseudomonas infections of the bronchi," British Medical Journal, 1:663-665 (1970).
Pines, A. et al., "Gentamicin and colistin in chronic purulent bronchial infections," British Medical Journal, 2:543-545 (1967).
Potter, B. P., "Aerosol antibiotic therapy in suppurative diseases of the lung and bronchi," Aerosol Antibiotic Therapy, 25:436-448 (1949).
Poyner, E. A. et al., "A comparative study on the pulmonary delivery of tobramycin encapsulated into liposomes and PLA microspheres following intravenous and endotracheal delivery," Journal of Controlled Release, 35(1):41-48 (1995).
Poyner, E. A. et al., "Preparation, properties and the effects of free and liposomal tobramycin on siderophore production by Pseudomonas aeruginosa," Journal of Antimicrobial Chemotherapy, 34:43-52 (1993).
Press Release, "Transave Announces Positive Phase II Results for Once-Daily Arikace in the Treatment of Cystic Fibrosis Patients Who Have Pseudomonas Lung Infections," Presented at the European Cystic Fibrosis Society Conference, Monmouth Junction, NJ, Jun. 13, 2008, 3 pages.
Price, C. I. et al., "Liposome delivery of aminoglycosides in burn wounds," Surgery, Gynecology & Obstetrics, 174:414-418 (1992).
Price, C. I. et al., "Liposome encapsulation: a method for enhancing the effectiveness of local antibiotics," Surgery, 115(4):480-487 (1994).

(56) References Cited

OTHER PUBLICATIONS

Price, C. I. et al., "Enhanced effectiveness of intraperitoneal antibiotics administered via liposomal carrier," Arch Surgery, 124:1411-1415 (1989).
Price, K. E. et al., "Amikacin, an aminoglycoside with marked activity against antibiotic-resistant clinical isolates," The Journal of Infectious Diseases, 134:S249-S261 (1976).
Ramsammy, L. S. et al., "The effect of gentamicin on the biophysical properties of phosphatidic acid liposomes is influenced by the O—C=O group of the lipid," Biochemistry, 27:8249-8254 (1988).
Ramsey, B. W. et al., "Intermittent administration of inhaled tobramycin in patients with cystic fibrosis. Cystic Fibrosis Inhaled Tobramycin Study Group," The New England Journal of Medicine, 340(1):23-30 (1999).
Ramsey, B. W. et al., "Efficacy of aerosolized tobramycin in patients with cystic fibrosis," The New England Journal of Medicine, 328:1740-1746 (1993).
Roehrborn, A. A. et al., "Lipid-based slow-release formulation of amikacin sulfate reduces foreign body-associated infections in mice," Antimicrobial Agents and Chemotherapy, 39(8):1752-1755 (1995).
Sabra, W. et al., "Physiological responses of pseudomonas aeruginosa PAO1 to oxidative stress in controlled microaerobic and aerobic cultures," Microbiology, 148:3195-3202 (2002).
Schentag, J. J., Antimicrobial action and pharmacokinetics/pharmacodynamics: the use of AUIC to improve efficacy and avoid resistance, Journal of Chemotherapy, 11(6):426-439 (1999).
Schiffelers, R. et al., "Liposome-encapsulated aminoglycosides in pre-clinical and clinical studies," Journal of Antimicrobial Chemotherapy, 48:333-344 (2001).
Schiffelers, R. M. et al., "Therapeutic efficacy of liposomal gentamicin in clinically relevant rat models," International Journal of Pharmaceutics, 214:103-105 (2001).
Schiffelers, R. M. et al., "In vivo synergistic interaction of liposomecoencapsulated gentamicin and ceftazidime," Journal Pharmacology Experimental Therapeutics, 298(1):369-375 (2001).
Schlegel, L. et al., "In-vitro killing activity of combinations of beta-lactam agents with aminoglycosides against penicillin-resistant pneumococci," The Journal of Antimicrobial Chemotherapy, 39(1):95-98 (1997).
Schreier, H. et al., "Pulmonary delivery of amikacin liposomes and acute liposome toxicity in the sheep," International Journal of Pharmaceutics, 87(1-3):183-193 (1992).
Schreier, H. et al., "Pulmonary delivery of liposomes," Journal of Controlled Release, 24(1):209-223 (1993).
Sermet-Gaudelus, I. et al., "Nebulized antibiotics in cystic fibrosis," Pediatric Drugs, 4(7):455-467 (2002).
Shah, S. P. et al., "Liposomal amikacin dry powder inhaler: effect of fines on in vitro performance," AAPS PharmSciTech, 5(4):e65:1-7 (2004).
Shima, K. et al., "A study of amikacin (BB-K8) on the clinical effects on the respiratory infection," Chemotherapy, 23(6):2128-2130 (1975) (with English Abstract).
Singh, P. K. et al., "Quorum-sensing signals indicate that cystic fibrosis lungs are infected with bacterial biofilms," Nature, 407:762-764 (2000).
Skubitz, K. M. et al., "Inhalational interleukin-2 liposomes for pulmonary metastases: a phase I clinical trial," Anti-Cancer Drugs, 11(7): 555-563 (2000).
Smith, A. L. et al., "Safety of aerosol tobramycin administration for 3 months to patients with cystic fibrosis," Pediatric Pulmonology, 7(4):265-271 (1989).
Stott, P. W. et al., "Characterization of complex coacervates of some tricyclic antidepressants and evaluation of their potential for enhancing transdermal flux," Journal of Controlled Release, 41(3):215-227 (1996).
Swenson, K. A. et al., "Pharmacokinetics and in vivo activity of liposome-encapsulated gentamicin," Antimicrobial Agents and Chemotherapy, 34(2)235-240 (1990).
Swenson, C. E. et al., "Liposomal aminoglycosides and TLC G-65," Aids Patient Care, pp. 290-296 (1991).
Szoka, F. Jr. et al., "Comparative properties and methods of preparation of lipid vesicles (liposomes)," Ann. Rev. Biophys. Bioeng., 9:467-508 (1980).
Takamoto, M. et al., "Imipenem/cilastatin sodium alone or combined with amikacin sulfate in respiratory infections," The Japanese Journal of Antibiotics, 47(9):1131-1144 (1994) (with English Abstract).
Tateda, K. et al., "Efficacy of beta-lactam antibiotics combined with gentamicin against penicillin-resistant pneumococcal pneumonia in CBA/J mice," The Journal of Antimicrobial Chemotherapy, 43(3):367-371 (1999).
Taylor, K. M. G. et al., "The influence of liposomal encapsulation on sodium cromoglycate pharmacokinetics in man," Pharmaceutical Research, 6(7):633-636 (1989).
Ten, R. M. et al., "Interleukin-2 liposomes for primary immune deficiency using the aerosol route," International Immunopharmacology, 2(2-3):333-344 (2002).
Terzano, C. et al., "Tobramycin aerosol: could the delivery system influence the particle size and deposition in the lower airways?" Recenti. Prog. Med., 89(5):245-249 (1998) (English Abstract).
Thomas, D. A. et al., "Acute effects of liposome aerosol inhalation on pulmonary function in healthy human volunteers," Chest, 99(5):1268-1270 (1991).
Thomasin, C. et al., "Drug microencapsulation by PLA/PLGA coacervation in the light of thermodynamics. 2. Parameters determining microsphere formation," Journal of Pharmaceutical Sciences, 87(3):269-275 (1998).
Trafny, E. A. et al., "Effects of free and liposome-encapsulated antibiotics on adherence of Pseudomonas aeruginosa to collagen type I," Antimicrobial Agents and Chemotherapy, 39(12):2645-2649 (1995).
Ulrich, A. S., "Biophysical aspects of using liposomes as delivery vehicles," Bioscience Reports, 22(2):129-150 (Apr. 2002).
Van Der Straeten, M. et al., "Amikacin in the treatment of gram-negative bronchopulmonary infections," The Journal of Infectious Diseases, 134:S391-S393 (1976).
Vecellio, L., "The mesh nebuliser: a recent technical innovation for aerosol delivery," Breathe, 2(3):253-260 (2006).
Veldhuizen, R. et al., "The role of lipids in pulmonary surfactant," Biochimica et Biophysica Acta, 1408:90-108 (1998).
Vidgren, M. et al., "A study of $^{99m}$ technetium-labelled beclomethasone dipropionate dilauroylphosphatidylcholine liposome aerosol in normal volunteers," International Journal of Pharmaceutics, 115:209-216 (1995).
Vitas, A. I. et al., "Effect of composition and method of preparation of liposomes on their stability and interaction with murine monocytes infected with *Brucella abortus*," Antimicrobial Agents and Chemotherapy, 40(1):146-151 (1996).
Wang, W. et al., "Research progress in pulmonary administration of liposome," Journal of Shenyang Pharmaceutical University, 17(3):226-229 (2000).
Westerman, E. M. et al., "Effect of nebulized colistin sulphate and colistin sulphomethate on lung function in patients with cystic fibrosis: a pilot study," Journal of Cystic Fibrosis, 3(1):23-28 (2004).
Whitehead, T. C. et al., "Kinetics and Toxicity of Liposomal and Conventional Amikacin in a Patient with Multidrug-Resistant Tuberculosis," Eur J Clin Microbiol. Infect. Dis., 17:794-797 (1998).
Wichert, B. V. et al., "Amikacin liposomes: characterization, aerosolization, and in vitro activity against *Mycobacterium avium—intracellulare* in alveolar macrophages," International Journal of Pharmaceutics, 78(1-3):227-235 (1992).
Wolff, R. K. et al., "Toxicologic testing of inhaled pharmaceutical aerosols," Critical Reviews in Toxicology, 23(4):343-369 (1993).
Worlitzsch, D. et al., "Effects of reduced mucus oxygen concentration in airway pseudomonas infections of cystic fibrosis patients," J. Clin. Invest., 109:317-325 (2002).
Xiu, L. et al., "Drug Resistant Analysis of Pseudomonas Aeruginosa in Patients with Mechanical Ventilation," Med. J. Chin. PLA, 27(6):544-545 (2002) (with English Abstract).

(56) References Cited

OTHER PUBLICATIONS

Yanagihara, K. et al., "Design of anti-bacterial drug and anti-Mycobacterial drug for drug delivery system," Current Pharmaceutical Design, 8:475-482 (2002).

Zeng, S. et al., "Intravitreal Pharmacokinetics of Liposome-encapsulated Amikacin in a Rabbit Model," Ophthamology, 100:1640-1644 (1993).

Zhang, J. H. et al., "A Novel Method to Prepare Liposomes Containing Amikacin," Journal Microencapsulation, 16(4):511-516 (1999).

Zhang, X. et al., "Antibacterial drug treatment of community acquired pneumonia," Chinese Journal of Respiratory and Critical Care Medicine, 4(4):258-260 (2005).

Zlatanov, Z. et al., "Gentamycin-pharmachim. Aerosol inhalation treatment of patients with chronic bronchitis," Medico Biologic Information 2, pp. 5-8 (1976).

Anacona et al., "Synthesis and antibacterial activity of metal complexes of ciprofloxacin," Transition Metal Chemistry (2001) 26:228-231.

Bruinenberg, P., "Safety, tolerability and pharmacokinetics of novel liposomal ciprofloxacin formulations for inhalation in healthy volunteers and in non-cystic bronchiectasis patients," Am. J. Respir. Crit. Care Med. (2010) 181:A3192.

Carter, G., "Characterization of biofilm formation by *Mycobacterium avium* strains," J. Med. Microbial. (2003) 52:747-752.

Chono, S, et al., "Influence of particle size on drug delivery to rat alveolar macrophages following pulmonary administration of ciprofloxacin incorporated into liposomes," Journal of Drug Targeting, 14(8):557-566 (2006).

Cipolla, D., "Development and Characterization of an In Vitro Release Assay for Liposomal Ciproftoxacin for Inhalation," J. Pharm. Sci., 103(1):314-327 (2014).

Cipolla, D., "Liposomal Formulations for Inhalation," Ther. Deliv., 4(8):1047-1072 (2013).

Conley et al., "Aerosol Delivery of Liposome-Encapsulated Ciprofloxacin: Aerosol Characterization and Efficacy against Francisella tularensis Infection in Mice," Antimicrobial Angents, 41(6):1288-1292 (Jun. 1997).

Desai et al., "A facile method of delivery of liposomes by nebulization," Journal of Controlled Release, 84:69-78 (2002).
Desai et al., "A Novel Approach to the Pulmonary Delivery of Liposomes in Dry Powder Form to Eliminate the Deleterious Effects of Milling," Journal of Pharmaceutical Sciences, 91(2):482-491 (Feb. 2002).
Elhissi et al., "Formulations generated from ethanol-based proliposomes for delivery via medical nebulizers," Journal of Pharmacy and Pharmacology, 58:887-894 (Jul. 2006).
Finlay, W. H. et al., "Regional lung deposition of nebulized liposome-encapsulated ciprofloxacin," International Journal of Pharmaceutics (Amsterdam), 167(1-2):121-127 (Jun. 1, 1998).
Hung et al., "Pharmacokinetics of Inhaled Liposome-encpasulated Fentanyl," Anesthesiology, 83(2):277-284 (Aug. 1995).
Kensil et al., "Alkaline Hydrolysis of Phospholipids in Model Membranes and the Dependence on Their State of Aggregation," Biochemistry, 20:6079-6085 (1981).
Kyriacos et al., "In Vitro Testing of Ciprofloxacin Formulations and Preliminary Study on BCS Biowaiver," Journal of Food and Drug Analysis, (2009) 17(2): 78-84.
Lasic et al., "Transmembrane gradient driven phase transitions within vesicles: lessons for drug delivery," Biochemica et Biophysica Acta, 1239:145-156 (1995).
Lasic, D. D., "Gelation of liposome interior: A novel method for drug encapsulation," FEBS Letters, 312(2.3):255-258 (Nov. 1992).
Lipuma, J. J., "Microbiological and immunologic considerations with aerosolized drug delivery," Chest. Sep. 2001;120(3 Suppl):118S-123S.
Moss, R. B., "Administration of aerosolized antibiotics in cystic fibrosis patients," Chest, 120(3 Suppl):107S-113S (Sep. 2001).
Piersimoni et al., "Pulmonary infections associated with non-tuberculous mycobacteria in immunocompetent patients," Lancet Infect Dis, 8:323-334 (2008).
Shek et al., "Liposomes in Pulmonary Applications: Physiochemical Considerations, Pulmonary Distribution and Antioxidant Delivery," Journal of Drug Targeting, 2:431-442 (1994).
Stark, B., "Long-term stability of sterically stabilized liposomes by freezing and freeze-drying: Effects of cryoprotectants on structure," Eur. J. Pharm. Sci. 41:546-555 (2010).
Strauss, G., "Stabilization of lipid bilayer by sucrose during freezing," PNAS (1986) 83:2422-2426.
Van Heeckeren, A et al., "Effects of bronchopulmonary inflammation induced by Pseudomonas aeruginosa on adenovirus-mediated gene transfer to airway epithelial cells in mice," Gene Ther., 5(3):345-351 (Mar. 1998).
Van Heeckeren, A. et al., "Delivery of CFTR by adenoviral vector to cystic fibrosis mouse lung in a model of chronic Pseudomonas aeruginosa lung infection," Am J Physiol Lung Cell Mol Physiol. Apr. 2004;286(4):L717-26. Epub Sep. 26, 2003.
Van Heeckeren, A. et al., "Effect of Pseudomonas infection on weight loss, lung mechanics, and cytokines in mice," Am J Respir Crit Care Med. Jan. 2000;161(1):271.
Van Heeckeren, A. et al., "Murine models of chronic Pseudomonas aeruginosa lung infection," Lab Anim., 36(3):291-312 (Jul. 2002).
Van Heeckeren, A. et al., "Role of CFTR genotype in the response to chronic Pseudomonas aeruginosa lung infection in mice," Am J Physiol Lung Cell Mol Physiol. Nov. 2004;287(5):L944-52. Epub Jul. 9, 2004.
Wang, Z. et al., "Improved drug delivery: Spray freeze dried nano-liposomal inhaled aerosols," Proceedings of the 2004 International Conference on MEMS, NANO and Smart Systems (ICMENS 2004), Badawy W. et al. (eds.), (University of Calgary), 1 page.
Weber, A. et al., "Nebulizer delivery of tobramycin to the lower respiratory tract," Pediatr Pulmonol., 17(5):331-339 (May 1994).
Wolkers, W. F. et al., "Preservation of dried liposomes in the presence of sugar and phosphate," Biochimica et Biophysica Acta, 1661:125-134 (2004).
Wong et al., "Liposome delivery of ciprofloxacin against intracellular Francisella tularensis infection," Journal of Controlled Release, 92:265-273 (2003).
Yamazaki, Y. et al., "The ability to form biofilm influences *Mycobacterium avium* invasion and translocation of bronchial epithelial cells," Cellular Microbiology, 8(5):806-814 (2006).
Zhigaltsev, I. V. et al., "Formation of drug-arylsulfonate complexes inside liposomes: A novel approach to improve drug retention," Journal of Controlled Release, 110:378-386 (2006). Available online Nov. 28, 2005.
Office Action for U.S. Appl. No. 14/987,508, mailed Apr. 1, 2016, 12 pages.
Ciofu, O. et al., "Occurrence of Hypermutable Pseudomonas aeruginosa in Cystic Fibrosis Patients is Associated with the Oxidative Stress Caused by Chronic Lung Inflammation," Antimicrobial Agents and Chemotherapy, 49(6):2276-2282, Jun. 2005.
Office Action for U.S. Appl. No. 15/093,180, mailed Jun. 24, 2016, 8 pages.
ClinicalTrials.gov, "Safety and Efficacy Study of Ciprofloxacin for Inhalation in Patients With Non-Cystic Fibrosis Bronchiectasis 'ORBIT-1'", Identifier: NCT00889967, First Received: Apr. 27, 2009, 3 pages.
Cymbala, A. A. et al., "The Disease-Modifying Effects of Twice-Weekly Oral Azithromycin in Patients with Bronchiectasis," Treat Respir. Med. 2005;4(2):117-122.
Jayaraman, S. et al., "Noninvasive in vivo fluorescence measurement of airway-surface liquid depth, salt concentration, and pH," J. Clin. Invest. 107:317-324 (2001).
Mercer, R. R. et al., "Cell Number and Distribution in Human and Rat Airways," Am. J. Respir. Cell Mol. Biol., vol. 10, pp. 613-624, 1994.
Rau, J. L. et al., "Performance Comparison of Nebulizer Designs: Constant-Output, Breath-Enhanced, and Dosimetric," Respir. Care 2004;49(2):174-179.

(56) References Cited

OTHER PUBLICATIONS

Tarran, R., "Regulation of Airway Surface Liquid Volume and Mucus Transport by Active Ion Transport," Proc. Am. Thorac. Soc., vol. 1, pp. 42-46, 2004.
Yim, D. et al., "The Development of Inhaled Liposome-Encapsulated Ciprofloxacin to Treat Cystic Fibrosis," Respiratory Drug Delivery, pp. 425-428 (2006).
Webb, M. S. et al., "Antibacterial Efficacy against an In Vivo *Salmonella typhimurium* Infection Model and Pharmacokinetics of a Liposomal Ciprofloxacin Formulation," Antimicrobial Agents and Chemotherapy, 42(1):45-52 (Jan. 1998).
Supplementary European Search Report for European Application No. 16156099.0, mailed Jul. 25, 2016, 7 pages.
Office Action for Canadian Application No. 2,896,083, mailed Jun. 3, 2016, 6 pages.
Office Action for U.S. Appl. No. 15/066,346, mailed Jul. 21, 2016, 9 pages.
Office Action for U.S. Appl. No. 15/066,360, mailed Jul. 20, 2016, 10 pages.
Schaad, U. B. et al., "Efficacy of inhaled amikacin as adjunct to intravenous combination therapy (ceftazidime and amikacin) in cystic fibrosis," Journal of Pediatrics, 111(4):599-605 (Oct. 1987).
Oh, Y-K et al., "Formulation and Efficacy of Liposome-Encapsulated Antibiotics for Therapy of Intracellular *Mycobacterium avium* Infection," Antimicrobial Agents and Chemotherapy, 39(9):2104-2111 (Sep. 1995).

\* cited by examiner

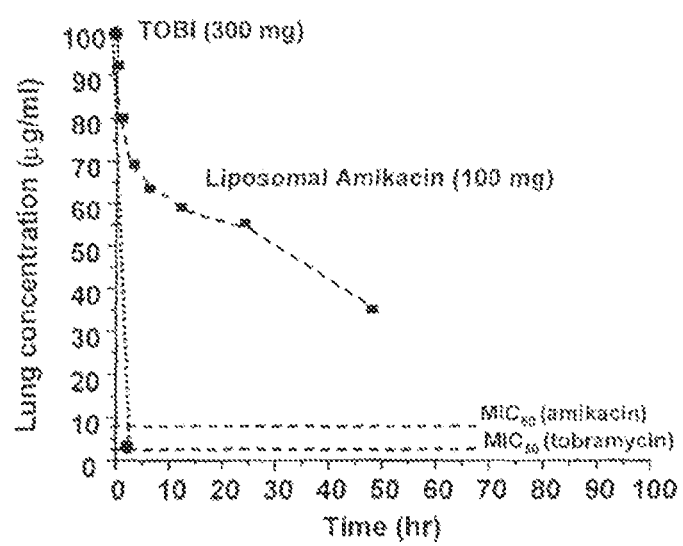

LIPID-BASED COMPOSITIONS OF ANTIINFECTIVES FOR TREATING PULMONARY INFECTIONS AND METHODS OF USE THEREOF

RELATED APPLICATIONS

This application is a continuation of U.S. application Ser. No. 14/987,508, filed Jan. 4, 2016, which is a continuation of U.S. application Ser. No. 14/080,922, filed Nov. 15, 2013, which is a continuation of U.S. application Ser. No. 13/666,420, filed Nov. 1, 2012, now U.S. Pat. No. 8,642,075, which is a continuation of U.S. application Ser. No. 13/527,213, filed Jun. 19, 2012, now U.S. Pat. No. 8,632,804, which is a continuation of U.S. application Ser. No. 11/634,343, filed Dec. 5, 2006, now U.S. Pat. No. 8,226,975, which claims the benefit of priority from U.S. Provisional Patent Application Ser. No. 60/748,468, filed Dec. 8, 2005, each of which is hereby incorporated by reference in its entirety.

BACKGROUND OF THE INVENTION

According to the World Health Organization, respiratory diseases are the number one cause of world-wide mortality; with at least 20% of the world's population afflicted. Over 25 million Americans have chronic lung disease, making it the number one disabler of American workers (>$50 B/yr), and the number three cause of mortality.

Currently, most infections are treated with oral or injectable antiinfectives, even when the pathogen enters through the respiratory tract. Often the antiinfective has poor penetration into the lung, and may be dose-limited due to systemic side-effects. Many of these issues can be overcome by local delivery of the antiinfective to the lungs of patients via inhalation. For example, inhaled tobramycin (TOBI®, Chiron Corp, Emeryville, Calif.), is a nebulized form of tobramycin, that has been shown to have improved efficacy and reduced nephro- and oto-toxicity relative to injectable aminoglycosides. Unfortunately, rapid absorption of the drug necessitates that the drug product be administered twice daily over a period of ca., 20 min per administration. For pediatrics and young adults with cystic fibrosis this treatment regimen can be taxing, especially when one takes into account the fact that these patients are on multiple time-consuming therapies. Any savings in terms of treatment times would be welcomed, and would likely lead to improvements in patient compliance. Achieving improved compliance with other patient populations (e.g., chronic obstructive pulmonary disease (COPD), acute bronchial exacerbations of chronic bronchitis) will be critically dependent on the convenience and efficacy of the treatment. Hence, it is an object of the present invention to improve patient compliance by providing formulations with sustained activity in the lungs. Sustained release formulations of antiinfectives are achieved by encapsulating the antiinfective in a liposome. Improving pulmonary targeting with sustained release formulations would further improve the therapeutic index by increasing local concentrations of drug and reducing systemic exposure. Improvements in targeting are also expected to reduce dose requirements.

Achieving sustained release of drugs in the lung is a difficult task, given the multiple clearance mechanisms that act in concert to rapidly remove inhaled drugs from the lung. These clearance methods include: (a) rapid clearance from the conducting airways over a period of hours by the mucociliary escalator; (b) clearance of particulates from the deep lung by alveolar macrophages; (c) degradation of the therapeutic by pulmonary enzymes, and; (d) rapid absorption of small molecule drugs into the systemic circulation. Absorption of small molecule drugs has been shown to be nearly quantitative, with an absorption time for hydrophilic small molecules of about 1 hr, and an absorption time for lipophilic drugs of about 1 min.

For TOBI® the absorption half-life from the lung is on the order of 1.5 hr. High initial peak concentrations of drug can lead to adaptive resistance, while a substantial time with levels below or near the effective minimum inhibitory concentration (MIC), may lead to selection of resistant phenotypes. It is hypothesized that keeping the level of antiinfective above the MIC for an extended period of time (i.e., eliminating sub-therapeutic trough levels) with a pulmonary sustained release formulation may reduce the potential for development of resistant phenotypes. Hence, it is a further object of the present invention to maintain the ratio of the area under the lung concentration/time curve to the MIC at 24 hr (i.e., the AUIC), not only at an adequate sustained therapeutic level, but above a critical level, so as to reduce the potential for selection of resistant strains.

It is assumed that only the "free" (un-encapsulated) drug has bactericidal activity. One potential disadvantage of liposomal sustained release formulations is that the encapsulation of drug in the liposomal formulation decreases the concentration of free drug reaching the lung pathogens, drug which is needed to achieve efficient killing of bacteria immediately following administration. Hence, it is further an object of the present invention to provide a formulation that contains sufficient free drug, to be bactericidal immediately following administration.

The disclosures of the foregoing are incorporated herein by reference in their entirety.

SUMMARY OF THE INVENTION

It is object of the present invention to use lipid-based composition encapsulation to improve the therapeutic effects of antiinfectives administered to an individual via the pulmonary route.

The subject invention results from the realization that administering a pharmaceutical composition comprising both free and liposome encapsulated antiinfective results in improved treatment of pulmonary infections.

In one aspect, the present invention relates to a system for treating or providing prophylaxis against a pulmonary infection, wherein the system comprises a pharmaceutical formulation comprising mixtures of free and lipid-based composition encapsulated antiinfective, wherein the amount of free antiinfective is sufficient to provide for immediate bactericidal activity, and the amount of encapsulated antiinfective is sufficient to provide sustained bactericidal activity, and reduce the development of resistant strains of the infectious agent, and an inhalation delivery device.

The free form of the antiinfective is available to provide a bolus of immediate antimicrobial activity. The slow release of antiinfective from the lipid-based composition following pulmonary administration is analogous to continuous administration of the antiinfective, thereby providing for sustained levels of antiinfective in the lungs. The sustained AUC levels provides prolonged bactericidal activity between administrations. Further, the sustained levels provided by the release of antiinfective from the lipid-based composition is expected to provide improved protection against the development of resistant microbial strains.

Combinations of free and encapsulated drug can be achieved by: (a) formulation of mixtures of free and encapsulated drug that are stable to the nebulization; (b) formulation of encapsulated drug which leads to burst on nebulization.

The ratio of free to encapsulated drug is contemplated to be between about 1:100 w:w and about 100:1 w:w, and may be determined by the minimum inhibitory concentration of the infectious agent and the sustained release properties of the formulation. The ratio of free to encapsulated drug can be optimized for a given infectious agent and drug formulation based on known pharmacodynamic targets for bacterial killing and prevention of resistance. Schentag, J. J. *J. Chemother.* 1999, 11, 426-439.

In a further embodiment, the present invention relates to the aforementioned system wherein the antiinfective is selected from the group consisting of antibiotic agents, antiviral agents, and antifungal agents. In a further embodiment, the antiinfective is an antibiotic selected from the group consisting of cephalosporins, quinolones, fluoroquinolones, penicillins, beta lactamase inhibitors, carbepenems, monobactams, macrolides, lincosamines, glycopeptides, rifampin, oxazolidonones, tetracyclines, aminoglycosides, streptogramins, and sulfonamides. In a further embodiment, the antiinfective is an aminoglycoside. In a further embodiment the antiinfective is amikacin, gentamicin, or tobramycin.

In a further embodiment, the lipid-based composition is a liposome. In a further embodiment, the liposome comprises a mixture of unilamellar vesicles and multilamellar vesicles. In a further embodiment, the liposome comprises a phospholipid and a sterol. In a further embodiment, the liposome comprises a phosphatidylcholine and a sterol. In a further embodiment, the liposome comprises dipalmitoylphosphatidylcholine (DPPC) and a sterol. In a further embodiment, the liposome comprises dipalmitoylphosphatidylcholine (DPPC) and cholesterol.

In a further embodiment, the present invention relates to the aforementioned system wherein the antiinfective is an aminogylcoside and the liposome comprises DPPC and cholesterol. In a further embodiment, the antiinfective is amikacin, the liposome comprises DPPC and cholesterol, and the liposome comprises a mixture of unilamellar vesicles and multilamellar vesicles.

In a further embodiment, the present invention relates to the aforementioned system, wherein the ratio by weight of free antiinfective to antiinfective encapsulated in a lipid-based composition is between about 1:100 and about 100:1. In a further embodiment, the ratio by weight is between about 1:10 and about 10:1. In a further embodiment, the ratio by weight is between about 1:2 and about 2:1.

In another embodiment, the present invention relates to a method for treating or providing prophylaxis against a pulmonary infection in a patient, the method comprising: administering an aerosolized pharmaceutical formulation comprising the antiinfective to the lungs of the patient, wherein the pharmaceutical formulation comprises mixtures of free and lipid-based composition encapsulated antiinfectives, and the amount of free antiinfective is sufficient to provide for bactericidal activity, and the amount of encapsulated antiinfective is sufficient to reduce the development of resistant strains of the infectious agent.

In a further embodiment, the aforementioned method comprises first determining the minimum inhibitory concentration (MIC) of an antiinfective for inhibiting pulmonary infections, and wherein the amount of free antiinfective is at least 2 times the MIC, preferably greater than 4 times the MIC, and preferably greater than 10 times the MIC of the antiinfective agent, where the MIC is defined as either the minimum inhibitory concentration in the epithelial lining of the lung, or alternatively the minimum inhibitory concentration in the solid tissue of the lung (depending on the nature of the infection).

In a further embodiment, the present invention relates to the aforementioned method, wherein the aerosolized pharmaceutical formulation is administered at least once per week.

In a further embodiment, the present invention relates to the aforementioned method, wherein the antiinfective is selected from the group consisting of antibiotic agents, antiviral agents, and antifungal agents. In a further embodiment, the antiinfective is an antibiotic selected from the group consisting of cephalosporins, quinolones, fluoroquinolones, penicillins, beta lactamase inhibitors, carbepenems, monobactams, macrolides, lincosamines, glycopeptides, rifampin, oxazolidonones, tetracyclines, aminoglycosides, streptogramins, and sulfonamides. In a further embodiment, the antiinfective is an aminoglycoside. In a further embodiment, the antiinfective is amikacin, gentamicin, or tobramycin.

In a further embodiment, the lipid-based composition is a liposome. In a further embodiment, the liposome encapsulated antiinfective comprises a phosphatidylcholine in admixture with a sterol. In a further aspect, the sterol is cholesterol. In a further aspect, the liposome encapsulated antiinfective comprises a mixture of unilamellar vesicles and multilamellar vesicles. In a further aspect, the liposome encapsulated antiinfective comprises a phosphatidylcholine in admixture with cholesterol, and wherein the liposome encapsulated antiinfective comprises a mixture of unilamellar vesicles and multilamellar vesicles.

The ratio of the area under the lung concentration/time curve to the MIC at 24 hr (i.e., the AUIC) is greater than 25, preferably greater than 100, and preferably greater than 250.

The therapeutic ratio of free/encapsulated drug and the required nominal dose can be determined with standard pharmacokinetic models, once the efficiency of pulmonary delivery and clearance of the drug product are established with the aerosol delivery device of choice.

In one aspect, the present invention relates to a method of treating a patient for a pulmonary infection comprising a cycle of treatment with lipid-based composition encapsulated antiinfective to enhance bacterial killing and reduce development of phenotypic resistance, followed by a cycle of no treatment to reduce the development of adaptive resistance. The treatment regimen may be determined by clinical research. In one embodiment, the treatment regime may be an on-cycle treatment for about 7, 14, 21, or 30 days, followed by an off-cycle absence of treatment for about 7, 14, 21, or 30 days.

In another aspect, the present invention relates to a method for reducing the loss of antiinfective encapsulated in lipid-based compositions upon nebulization comprising administering the antiinfective encapsulated in lipid-based compositions with free antiinfective.

The systems and methods of the present invention are useful for treating, for example, lung infections in cystic fibrosis patients, chronic obstructive pulmonary disease (COPD), bronchiectasis, acterial pneumonia, and in acute bronchial exacerbations of chronic bronchitis (ABECB). In addition, the technology is useful in the treatment of intracellular infections including Mycobacterium tuberculosis, and inhaled agents of bioterror (e.g., anthrax and tularemia). The technology may also be used as a phophylactic agent to treat opportunistic fungal infections (e.g., aspergillosis) in immunocompromised patients (e.g., organ transplant or AIDS patients).

With bacteria and other infective agents becoming increasingly resistant to traditional treatments, new and more effective treatments for infective agent related illnesses are needed. The present invention addresses these issues by providing a system comprising a pharmaceutical composition comprising both free and lipid-based composition encapsulated antiinfective and an inhalation device. Formulating the antiinfective as a mixture of free and lipid-based composition encapsulated antiinfective provides several advantages, some of which include: (a) provides for a bolus of free antiinfective for immediate bactericidal activity and a sustained level of antiinfective for prevention of resistance; (b) simplifies the manufacturing process, as less free antiinfective need be removed via diafiltration; and (c) allows for greater antiinfective contents to be achieved in the drug product.

These embodiments of the present invention, other embodiments, and their features and characteristics, will be apparent from the description, drawings and claims that follow.

BRIEF DESCRIPTION OF THE DRAWINGS

FIG. 1 depicts the plot of lung concentration (μg/ml) as a function of time following nebulization of unencapsulated tobramycin at a nominal dose of 300 mg (TOBI®, Chiron Corp., Emeryville, Calif.), and liposomal amikacin at a nominal dose of 100 mg. Lung concentrations for both drug products are calculated assuming a volume of distribution for aminoglycosides in the lung of 200 ml. The tobramycin curve was determined by pharmacokinetic modeling of the temporal tobramycin plasma concentration curve (Le Brun thesis, 2001).

DETAILED DESCRIPTION OF THE INVENTION

Definitions

For convenience, before further description of the present invention, certain terms employed in the specification, examples and appended claims are collected here. These definitions should be read in light of the remainder of the disclosure and understood as by a person of skill in the art. Unless defined otherwise, all technical and scientific terms used herein have the same meaning as commonly understood by a person of ordinary skill in the art.

The articles "a" and "an" are used herein to refer to one or to more than one (i.e. to at least one) of the grammatical object of the article. By way of example, "an element" means one element or more than one element.

The term "antibacterial" is art-recognized and refers to the ability of the compounds of the present invention to prevent, inhibit or destroy the growth of microbes of bacteria.

The terms "antiinfective" and "antiinfective agent" are used interchangeably throughout the specification to describe a biologically active agent which can kill or inhibit the growth of certain other harmful pathogenic organisms, including but not limited to bacteria, yeasts and fungi, viruses, protozoa or parasites, and which can be administered to living organisms, especially animals such as mammals, particularly humans.

The term "antimicrobial" is art-recognized and refers to the ability of the compounds of the present invention to prevent, inhibit or destroy the growth of microbes such as bacteria, fungi, protozoa and viruses.

The term "bioavailable" is art-recognized and refers to a form of the subject invention that allows for it, or a portion of the amount administered, to be absorbed by, incorporated to, or otherwise physiologically available to a subject or patient to whom it is administered.

The terms "comprise" and "comprising" are used in the inclusive, open sense, meaning that additional elements may be included.

The term "illness" as used herein refers to any illness caused by or related to infection by an organism.

The term "including" is used herein to mean "including but not limited to". "Including" and "including but not limited to" are used interchangeably.

The term "lipid-based composition" as used herein refers to compositions that primarily comprise lipids. Non-limiting examples of lipid-based compositions may take the form of coated lipid particles, liposomes, emulsions, micelles, and the like.

The term "mammal" is known in the art, and exemplary mammals include humans, primates, bovines, porcines, canines, felines, and rodents (e.g., mice and rats).

The term "microbe" is art-recognized and refers to a microscopic organism. In certain embodiments the term microbe is applied to bacteria. In other embodiments the term refers to pathogenic forms of a microscopic organism.

A "patient," "subject" or "host" to be treated by the subject method may mean either a human or non-human animal.

The term "pharmaceutically-acceptable salts" is art-recognized and refers to the relatively non-toxic, inorganic and organic acid addition salts of compounds, including, for example, those contained in compositions of the present invention.

The term "prodrug" is art-recognized and is intended to encompass compounds which, under physiological conditions, are converted into the antibacterial agents of the present invention. A common method for making a prodrug is to select moieties which are hydrolyzed under physiological conditions to provide the desired compound. In other embodiments, the prodrug is converted by an enzymatic activity of the host animal or the target bacteria.

The term "treating" is art-recognized and refers to curing as well as ameliorating at least one symptom of any condition or disease.

Lipids

The lipids used in the pharmaceutical formulations of the present invention can be synthetic, semi-synthetic or naturally-occurring lipids, including phospholipids, tocopherols, sterols, fatty acids, glycoproteins such as albumin, negatively-charged lipids and cationic lipids. In terms of phosholipids, they could include such lipids as egg phosphatidylcholine (EPC), egg phosphatidylglycerol (EPG), egg phosphatidylinositol (EPI), egg phosphatidylserine (EPS), phosphatidylethanolamine (EPE), and phosphatidic acid (EPA); the soya counterparts, soy phosphatidylcholine (SPC); SPG, SPS, SPI, SPE, and SPA; the hydrogenated egg and soya counterparts (e.g., HEPC, HSPC), other phospholipids made up of ester linkages of fatty acids in the 2 and 3 of glycerol positions containing chains of 12 to 26 carbon atoms and different head groups in the I position of glycerol that include choline, glycerol, inositol, serine, ethanolamine, as well as the corresponding phosphatidic acids. The chains on these fatty acids can be saturated or unsaturated, and the phospholipid may be made up of fatty acids of different chain lengths and different degrees of unsaturation. In particular, the compositions of the formulations can include dipalmitoylphosphatidylcholine (DPPC), a major constituent of naturally-occurring lung surfactant. Other examples include dimyristoylphosphatidycholine (DMPC) and dimyristoylphosphatidylglycerol (DMPG) dipalmitoylphosphatidcholine (DPPQ and dipalmitoylphosphatidylglycerol (DPPG) distearoylphosphatidylcholine (DSPQ and distearoylphosphatidylglycerol (DSPG), dioleylphosphatidylethanolamine (DOPE) and mixed phospholipids like palmitoylstearoylphosphatidyl-choline (PSPC) and palmiloylstearolphosphatidylglycerol (PSPG), and single acylated phospholipids like mono-oleoyl-phosphatidylethanolamine (MOPE).

The sterols can include, cholesterol, esters of cholesterol including cholesterol hemi-succinate, salts of cholesterol including cholesterol hydrogen sulfate and cholesterol sulfate, ergosterol, esters of ergosterol including ergosterol hemi-succinate, salts of ergosterol including ergosterol hydrogen sulfate and ergosterol sulfate, lanosterol, esters of lanosterol including lanosterol hemi-succinate, salts of lanosterol including lanosterol hydrogen sulfate and lanosterol sulfate. The tocopherols can include tocopherols, esters of tocopherols including tocopherol hemi-succinates, salts of tocopherols including tocopherol hydrogen sulfates and tocopherol sulfates. The term "sterol compound" includes sterols, tocopherols and the like.

The cationic lipids used can include ammonium salts of fatty acids, pholids and glycerides. The fatty acids include fatty acids of carbon chain lengths of 12 to 26 carbon atoms that are either saturated or unsaturated. Some specific examples include: myristylamine, palmitylamine, laurylamine and stearylamine, dilauroyl ethylphosphocholine (DLEP), dimyristoyl ethylphosphocholine (DMEP), dipalmitoyl ethylphosphocholine (DPEP) and distearoyl ethylphosphocholine (DSEP), N-(2,3-di-(9-(Z)-octadecenyloxy)-prop-1-yl-N,N,N-trimethylammonium chloride (DOTMA) and 1,2-bis(oleoyloxy)-3-(trimethylammonio) propane (DOTAP).

The negatively-charged lipids which can be used include phosphatidyl-glycerols (PGs), phosphatidic acids (PAs), phosphatidylinositols (PIs) and the phosphatidyl serines (PSs). Examples include DMPG, DPPG, DSPG, DMPA, DPPA, DSPA, DMPI, DPPI, DSPI, DMPS, DPPS and DSPS.

Phosphatidylcholines, such as DPPC, aid in the uptake by the cells in the lung (e.g., the alveolar macrophages) and helps to sustain release of the bioactive agent in the lung. The negatively charged lipids such as the PGs, PAs, PSs and PIs, in addition to reducing particle aggregation, are believed to play a role in the sustained release characteristics of the inhalation formulation as well as in the transport of the formulation across the lung (transcytosis) for systemic uptake. The sterol compounds are believed to affect the release characteristics of the formulation.

Liposomes

Liposomes are completely closed lipid bilayer membranes containing an entrapped aqueous volume. Liposomes may be unilamellar vesicles (possessing a single membrane bilayer) or multilamellar vesicles (onion-like structures characterized by multiple membrane bilayers, each separated from the next by an aqueous layer). The bilayer is composed of two lipid monolayers having a hydrophobic "tail" region and a hydrophilic "head" region. The structure of the membrane bilayer is such that the hydrophobic (nonpolar) "tails" of the lipid monolayers orient toward the center of the bilayer while the hydrophilic "heads" orient towards the aqueous phase.

Liposomes can be produced by a variety of methods (for a review, see, e.g., Cullis et al. (1987)). Bangham's procedure (J. Mol. Biol. (1965)) produces ordinary multilamellar vesicles (MLVs). Lenk et al. (U.S. Pat. Nos. 4,522,803, 5,030,453 and 5,169,637). Fountain et al. (U.S. Pat. No. 4,588,578) and Cullis et al. (U.S. Pat. No. 4,975,282) disclose methods for producing multilamellar liposomes having substantially equal interlamellar solute distribution in each of their aqueous compartments. Paphadjopoulos et al., U.S. Pat. No. 4,235,871, discloses preparation of oligolamellar liposomes by reverse phase evaporation.

Unilamellar vesicles can be produced from MLVs by a number of techniques, for example, the extrusion of Cullis et al. (U.S. Pat. No. 5,008,050) and Loughrey et al. (U.S. Pat. No. 5,059,421)). Sonication and homogenization cab be so used to produce smaller unilamellar liposomes from larger liposomes (see, for example, Paphadjopoulos et al. (1968); Deamer and Uster (1983); and Chapman et al. (1968)).

The original liposome preparation of Bangham et al. (J. Mol. Biol., 1965, 13:238-252) involves suspending phospholipids in an organic solvent which is then evaporated to dryness leaving a phospholipid film on the reaction vessel. Next, an appropriate amount of aqueous phase is added, the 60 mixture is allowed to "swell", and the resulting liposomes which consist of multilamellar vesicles (MLVs) are dispersed by mechanical means. This preparation provides the basis for the development of the small sonicated unilamellar vesicles described by Papahadjopoulos et al. (Biochim. Biophys, Acta., 1967, 135:624-638), and large unilamellar vesicles.

Techniques for producing large unilamellar vesicles (LUVs), such as, reverse phase evaporation, infusion procedures, and detergent dilution, can be used to produce liposomes. A review of these and other methods for producing liposomes may be found in the text Liposomes. Marc Ostro, ed., Marcel Dekker, Inc., New York, 1983, Chapter 1, the pertinent portions of which are incorporated herein by reference. See also Szoka, Jr. et al., (1980, Ann. Rev. Biophys. Bioeng., 9:467), the pertinent portions of which are also incorporated herein by reference.

Other techniques that are used to prepare vesicles include those that form reverse-phase evaporation vesicles (REV), Papahadjopoulos et al., U.S. Pat. No. 4,235,871. Another class of liposomes that may be used are those characterized as having substantially equal lamellar solute distribution. This class of liposomes is denominated as stable plurilamellar vesicles (SPLV) as defined in U.S. Pat. No. 4,522,803 to Lenk, et al. and includes monophasic vesicles as described in U.S. Pat. No. 4,588,578 to Fountain, et al. and frozen and thawed multilamellar vesicles (FATMLV) as described above.

A variety of sterols and their water soluble derivatives such as cholesterol hemisuccinate have been used to form liposomes; see specifically Janoff et al., U.S. Pat. No. 4,721,612, issued Jan. 26, 1988, entitled "Steroidal Liposomes." Mayhew et al., PCT Publication No. WO 85/00968, published Mar. 14, 1985, described a method for reducing the toxicity of drugs by encapsulating them in liposomes comprising alpha-tocopherol and certain derivatives thereof. Also, a variety of tocopherols and their water soluble derivatives have been used to form liposomes, see Janoff et al., PCT Publication No. 87/02219, published Apr. 23, 1987, entitled "Alpha Tocopherol-Based Vesicles".

The liposomes are comprised of particles with a mean diameter of approximately 0.01 microns to approximately 3.0 microns, preferably in the range about 0.2 to 1.0 microns. The sustained release property of the liposomal product can be regulated by the nature of the lipid membrane and by inclusion of other excipients (e.g., sterols) in the composition.

Infective Agent

The infective agent included in the scope of the present invention may be a bacteria. The bacteria can be selected from: *Pseudomonas aeruginosa, Bacillus anthracis, Listeria monocytogenes, Staphylococcus aureus, Salmonellosis, Yersina pestis, Mycobacterium leprae, M. africanum, M. asiaticum, M. avium-intracellulaire, M. chelonei abscessus, M. fallax, M. fortuitum, M. kansasii, M. leprae, M. mainoense, M. shimoidei, M. simiae, M. szulgai, M. xenopi, M. tuberculosis, Brucella melitensis, Brucella suis, Brucella abortus, Brucella canis, Legionella pneumonophilia, Francisella tularensis, Pneumocystis carinii, mycoplasma,* and *Burkholderia cepacia.*

The infective agent included in the scope of the present invention can be a virus. The virus can be selected from: hantavirus, respiratory syncytial virus, influenza, and viral pneumonia.

The infective agent included in the scope of the present invention can be a fungus. Fungal diseases of note include: aspergillosis, disseminated candidiasis, blastomycosis, coccidioidomycosis, cryptococcosis, histoplasmosis, mucormycosis, and sporotrichosis.

Antiinfectives

The term antiinfective agent is used throughout the specification to describe a biologically active agent which can kill or inhibit the growth of certain other harmful pathogenic organisms, including but not limited to bacteria, yeasts and fungi, viruses, protozoa or parasites, and which can be administered to living organisms, especially animals such as mammals, particularly humans.

Non-limiting examples of antibiotic agents that may be used in the antiinfective compositions of the present invention include cephalosporins, quinolones and fluoroquinolones, penicillins, and beta lactamase inhibitors, carbepenems, monobactams, macrolides and lincosamines, glycopeptides, rifampin, oxazolidonones, tetracyclines, aminoglycosides, streptogramins, sulfonamides, and others. Each family comprises many members.

Cephalosporins

Cephalosporins are further categorized by generation. Non-limiting examples of cephalosporins by generation include the following. Examples of cephalosporins I generation include Celadroxil, Cefazolin, Cephalexin, Cephalothin, Cephapirin, and Cephradine. Examples of cephalosporins II generation include Cefaclor, Cefamandol, Cefonicid, Cefotetan, Cefoxitin, Cefprozil, Ceftmetazole, Cefuroxime, Cefuroxime axetil, and Loracarbef. Examples of cephalosporins III generation include Cefdinir, Ceftibuten, Cefditoren, Cefetamet, Cefpodoxime, Celprozil, Cefuroxime (axetil), Cefuroxime (sodium), Cefoperazone, Cefixime, Cefotaxime, Cefpodoxime proxetil, Ceftazidime, Ceftizoxime, and Ceftriaxone. Examples of cephalosporins IV generation include Cefepime.

Quinolones and Fluoroquinolones

Non-limiting examples of quinolones and fluoroquinolones include Cinoxacin, Ciprofloxacin, Enoxacin, Gatifloxacin, Grepafloxacin, Levofloxacin, Lomefloxacin, Moxifloxacin, Nalidixic acid, Norfloxacin, Ofloxacin, Sparfloxacin, Trovafloxacin, Oxolinic acid, Gemifloxacin, and Perfloxacin.

Penicillins

Non-limiting examples of penicillins include Amoxicillin, Ampicillin, Bacampicillin, Carbenicillin Indanyl, Mezlocillin, Piperacillin, and Ticarcillin.

Penicillins and Beta Lactamase Inhibitors

Non-limiting examples of penicillins and beta lactamase inhibitors include Amoxicillin-Clavulanic Acid, Ampicillin-Sulbactam, Sulfactam, Tazobactam, Benzylpenicillin, Cloxacillin, Dicloxacillin, Methicillin, Oxacillin, Penicillin G (Benzathine, Potassium, Procaine), Penicillin V, Penicillinase-resistant penicillins, Isoxazoylpenicillins, Aminopenicillins, Ureidopenicillins, Piperacillin+Tazobactam, Ticarcillin+Clavulanic Acid, and Nafcillin.

Carbepenems

Non-limiting examples of carbepenems include Imipenem-Cilastatin and Meropenem.

Monobactans

A non-limiting example of a monobactam includes Aztreonam.

Macrolides and Lincosamines

Non-limiting examples of macrolides and lincosamines include Azithromycin, Clarithromycin, Clindamycin, Dirithromycin, Erythromycin, Lincomycin, and Troleandomycin.

Glycopeptides

Non-limiting examples of glycopeptides include Teicoplanin and Vancomycin.

Rifampin

Non-limiting examples of rifampins include Rifabutin, Rifampin, and Rifapentine.

Oxazolidonones

A non-limiting example of oxazolidonones includes Linezolid.

Tetracyclines

Non-limiting examples of tetracyclines include Demeclocycline, Doxycycline, Methacycline, Minocycline, Oxytetracycline, Tetracycline, and Chlortetracycline.

Aminoglycosides

Non-limiting examples of aminoglycosides include Amikacin, Gentamicin, Kanamycin, Neomycin, Netilmicin, Streptomycin, Tobramycin, and Paromomycin.

Streptogramins

A non-limiting example of streptogramins includes Quinopristin+Dalfopristin.

Sulfonamides

Non-limiting examples of sulfonamides include Mafenide, Silver Sulfadiazine, Sulfacetamide, Sulfadiazine, Sulfamethoxazole, Sulfasalazine, Sulfisoxazole, Trimethoprim-Sulfmethoxazole, and Sulfamethizole.

Others

Non-limiting examples of other antibiotic agents include Bacitracin, Chloramphenicol, Colistemetate, Fosfomycin, Isoniazid, Methenamine, Metronidazol, Mupirocin, Nitrofurantoin, Nitrofurazone, Novobiocin, Polymyxin B, Spectinomycin, Trimethoprine, Trimethoprine/Sulfamethoxazole, Cationic peptides, Colistin, Iseganan, Cycloserine, Capreomycin, Pyrazinamide, Para-aminosalicyclic acid, and Erthromycin ethylsuccinate+sulfisoxazole.

Antiviral agents include, but are not limited to: zidovudine, acyclovir, ganciclovir, vidarabine, idoxuridine, trifluridine, ribavirin, interferon alpha-2a, interferon alpha-2b, interferon beta, interferon gamma).

Antifungal agents include, but are not limited to: amphotericin B, nystatin, hamycin, natamycin, pimaricin, ambruticin, itraconazole, terconazole, ketoconazole, voriconazole, miconazole, nikkomycion Z, griseofulvin, candicidin, cilofungin, chlotrimazole, clioquinol, caspufungin, tolnaflate.

Dosages

The dosage of any compositions of the present invention will vary depending on the symptoms, age and body weight of the patient, the nature and severity of the disorder to be treated or prevented, the route of administration, and the form of the subject composition. Any of the subject formulations may be administered in a single dose or in divided doses. Dosages for the compositions of the present invention may be readily determined by techniques known to those of skill in the art or as taught herein.

In certain embodiments, the dosage of the subject compounds will generally be in the range of about 0.01 ng to about 10 g per kg body weight, specifically in the range of about 1 ng to about 0.1 g per kg, and more specifically in the range of about 100 ng to about 10 mg per kg.

An effective dose or amount, and any possible affects on the timing of administration of the formulation, may need to be identified for any particular composition of the present invention. This may be accomplished by routine experiment as described herein, using one or more groups of animals (preferably at least 5 animals per group), or in human trials if appropriate. The effectiveness of any subject composition and method of treatment or prevention may be assessed by administering the composition and assessing the effect of the administration by measuring one or more applicable indices, and comparing the post-treatment values of these indices to the values of the same indices prior to treatment.

The precise time of administration and amount of any particular subject composition that will yield the most effective treatment in a given patient will depend upon the activity, pharmacokinetics, and bioavailability of a subject composition, physiological condition of the patient (including age, sex, disease type and stage, general physical condition, responsiveness to a given dosage and type of medication), route of administration, and the like. The guidelines presented herein may be used to optimize the treatment, e.g., determining the optimum time and/or amount of administration, which will require no more than routine experimentation consisting of monitoring the subject and adjusting the dosage and/or timing.

While the subject is being treated, the health of the patient may be monitored by measuring one or more of the relevant indices at predetermined times during the treatment period. Treatment, including composition, amounts, times of administration and formulation, may be optimized according to the results of such monitoring. The patient may be periodically reevaluated to determine the extent of improvement by measuring the same parameters. Adjustments to the amount(s) of subject composition administered and possibly to the time of administration may be made based on these reevaluations.

Treatment may be initiated with smaller dosages which are less than the optimum dose of the compound. Thereafter, the dosage may be increased by small increments until the optimum therapeutic effect is attained.

The use of the subject compositions may reduce the required dosage for any individual agent contained in the compositions (e.g., the Fab1 inhibitor) because the onset and duration of effect of the different agents may be complimentary.

Toxicity and therapeutic efficacy of subject compositions may be determined by standard pharmaceutical procedures in cell cultures or experimental animals, e.g., for determining the $LD_{50}$ and the $ED_{50}$.

The data obtained from the cell culture assays and animal studies may be used in formulating a range of dosage for use in humans. The dosage of any subject composition lies preferably within a range of circulating concentrations that include the $ED_{50}$ with little or no toxicity. The dosage may vary within this range depending upon the dosage form employed and the route of administration utilized. For compositions of the present invention, the therapeutically effective dose may be estimated initially from cell culture assays.

Pharmaceutical Formulation

The pharmaceutical formulation of the antiinfective may be comprised of either an aqueous dispersion of liposomes and free antiinfective, or a dehydrated powder containing liposomes and free antiinfective. The formulation may contain lipid excipients to form the liposomes, and salts/buffers to provide the appropriate osmolarity and pH. The dry powder formulations may contain additional excipients to prevent the leakage of encapsulated antiinfective during the drying and potential milling steps needed to create a suitable particle size for inhalation (i.e., 1-5 μm). Such excipients are designed to increase the glass transition temperature of the antiinfective formulation. The pharmaceutical excipient may be a liquid or solid filler, diluent, solvent or encapsulating material, involved in carrying or transporting any subject composition or component thereof from one organ, or portion of the body, to another organ, or portion of the body. Each excipient must be "acceptable" in the sense of being compatible with the subject composition and its components and not injurious to the patient. Suitable excipients include trehalose, raffinose, mannitol, sucrose, leucine, trileucine, and calcium chloride. Examples of other suitable excipients include (1) sugars, such as lactose, and glucose; (2) starches, such as corn starch and potato starch; (3) cellulose, and its derivatives, such as sodium carboxymethyl cellulose, ethyl cellulose and cellulose acetate; (4) powdered tragacanth; (5) malt; (6) gelatin; (7) talc; (8) excipients, such as cocoa butter and suppository waxes; (9) oils, such as peanut oil, cottonseed oil, safflower oil, sesame oil, olive oil, corn oil and soybean oil; (10) glycols, such as propylene glycol; (11) polyols, such as glycerin, sorbitol, and polyethylene glycol; (12) esters, such as ethyl oleate and ethyl laurate; (13) agar; (14) buffering agents, such as magnesium hydroxide and aluminum hydroxide; (15) alginic acid; (16) pyrogen-free water; (17) isotonic saline; (18) Ringer's solution; (19) ethyl alcohol; (20) phosphate buffer solutions; and (21) other non-toxic compatible substances employed in pharmaceutical formulations.

Inhalation Device

The pharmaceutical formulations of the present invention may be used in any dosage dispensing device adapted for intranasal administration. The device should be constructed with a view to ascertaining optimum metering accuracy and compatibility of its constructive elements, such as container, valve and actuator with the nasal formulation and could be based on a mechanical pump system, e.g., that of a metered-dose nebulizer, dry powder inhaler, soft mist inhaler, or a nebulizer. Due to the large administered dose, preferred devices include jet nebulizers (e.g., PARI LC Star, AKITA), soft mist inhalers (e.g., PARI e-Flow), and capsule-based dry powder inhalers (e.g., PH&T Turbospin). Suitable propellants may be selected among such gases as fluorocarbons, hydrocarbons, nitrogen and dinitrogen oxide or mixtures thereof.

The inhalation delivery device can be a nebulizer or a metered dose inhaler (MDI), or any other suitable inhalation delivery device known to one of ordinary skill in the art. The device can contain and be used to deliver a single dose of the antiinfective compositions or the device can contain and be used to deliver multi-doses of the compositions of the present invention.

A nebulizer type inhalation delivery device can contain the compositions of the present invention as a solution, usually aqueous, or a suspension. In generating the nebulized spray of the compositions for inhalation, the nebulizer type delivery device may be driven ultrasonically, by compressed air, by other gases, electronically or mechanically. The ultrasonic nebulizer device usually works by imposing a rapidly oscillating waveform onto the liquid film of the formulation via an electrochemical vibrating surface. At a given amplitude the waveform becomes unstable, whereby it disintegrates the liquids film, and it produces small droplets of the formulation. The nebulizer device driven by air or other gases operates on the basis that a high pressure gas stream produces a local pressure drop that draws the liquid formulation into the stream of gases via capillary action. This fine liquid stream is then disintegrated by shear forces. The nebulizer may be portable and hand held in design, and may be equipped with a self contained electrical unit. The nebulizer device may comprise a nozzle that has two coincident outlet channels of defined aperture size through which the liquid formulation can be accelerated. This results in impaction of the two streams and atomization of the formulation. The nebulizer may use a mechanical actuator to force the liquid formulation through a multiorifice nozzle of defined aperture size(s) to produce an aerosol of the formulation for inhalation. In the design of single dose nebulizers, blister packs containing single doses of the formulation may be employed.

In the present invention the nebulizer may be employed to ensure the sizing of particles is optimal for positioning of the particle within, for example, the pulmonary membrane.

A metered dose inhalator (MDI) may be employed as the inhalation delivery device for the compositions of the present invention. This device is pressurized (pMDI) and its basic structure comprises a metering valve, an actuator and a container. A propellant is used to discharge the formulation from the device. The composition may consist of particles of a defined size suspended in the pressurized propellant(s) liquid, or the composition can be in a solution or suspension of pressurized liquid propellant(s). The propellants used are primarily atmospheric friendly hydroflourocarbons (HFCs) such as 134a and 227. Traditional chloroflourocarbons like CFC-11, 12 and 114 are used only when essential. The device of the inhalation system may deliver a single dose via, e.g., a blister pack, or it may be multi dose in design. The pressurized metered dose inhalator of the inhalation system can be breath actuated to deliver an accurate dose of the lipid-containing formulation. To insure accuracy of dosing, the delivery of the formulation may be programmed via a microprocessor to occur at a certain point in the inhalation cycle. The MDI may be portable and hand held.

EXEMPLIFICATION

Example 1

Pharmacokinetics of amikacin delivered as both free and encapsulated amikacin in healthy volunteers. The nebulized liposomal amikacin contains a mixture of encapsulated (ca., 60%) and free amikacin (ca., 40%). Following inhalation in healthy volunteers the corrected nominal dose was 100 mg as determined by gamma scintigraphy. FIG. 1 depicts the lung concentration of amikacin and TOBI® (administered 100% free), based on pharmacokinetic modeling of serum concentrations over time. Both curves assume a volume of distribution for aminoglycosides in the lung of 200 ml. Interestingly, the peak levels of antiinfective in the lung are approximately equivalent for the 100 mg dose of liposomal amikacin, and the 300 mg dose of TOBI®. This is a consequence of the rapid clearance of the free tobramycin from the lung by absorption into the systemic circulation with a half-life of about 1.5 hr. These results serve as a demonstration of the improved lung targeting afforded by liposomal encapsulation. The presence of free and encapsulated antiinfective in the amikacin formulation is demonstrated by the two component pharmacokinetic profile observed. Free amikacin is rapidly absorbed into the systemic circulation (with a half-life similar to TOBI), while the encapsulated drug has a lung half-life of approximately 45 hr. The free amikacin is available to provide bactericidal activity, while the encapsulated drug provides sustained levels of drug in the lung, enabling improved killing of resistant bacterial strains. The measured lung concentrations for the liposomal compartment are significantly above the $MIC_{50}$ of 1240 clinical isolates of *Pseudomonas aeruginosa*, potentially reducing the development of resistance.

Example 2

Impact of free amikacin on the percentage of amikacin encapsulated in liposomes following nebulization. Liposomal preparations of amikacin may exhibit significant leakage of encapsulated drug during nebulization. As detailed in Table 1 below, the presence of free amikacin in solution was shown to surprisingly decrease the leakage of antiinfective by about four-fold from the liposome. While not wishing to be limited to any particular theory, it is hypothesized that liposomes break-up and re-form during nebulization, losing encapsulated antiinfective in the process. Alternatively, encapsulated antiinfective is lost during nebulization because the liposome membrane becomes leaky. When an excess of free antiinfective is present in solution, the free antiinfective is readily available in close proximity to the liposome, and is available to be taken back up into the liposome on re-formation.

TABLE 1

Effect of free amikacin on the leakage of amikacin from liposome-encapsulated amikacin.

| Formulation | % Free Amikacin (Pre-nebulization) | % Free Amikacin (Post-nebulization) | % Free Amikacin (Due to nebulization) |
| --- | --- | --- | --- |
| A | 3.3 (n = 1) | 42.4 ± 3.2 (n = 3) | 39.1 ± 3.2 (n = 3) |
| B | 53.6 ± 5.4 (n = 9) | 63.3 ± 4.7 (n = 9) | 9.8 ± 5.8 (n = 9) |

Wherein n is the number of measurements.

INCORPORATION BY REFERENCE

All of the patents and publications cited herein are hereby incorporated by reference.

EQUIVALENTS

Those skilled in the art will recognize, or be able to ascertain using no more than routine experimentation, many equivalents to the specific embodiments of the invention described herein. Such equivalents are intended to be encompassed by the following claims.

I claim:

1. A pharmaceutical formulation comprising a mixture of free quinolone antibiotic agent, a quinolone antibiotic agent encapsulated in a plurality of liposomes, and a pharmaceutical excipient, wherein the formulation is a solution or a suspension, the ratio by weight of the free quinolone antibiotic agent to the encapsulated quinolone antibiotic agent is between about 1:10 and about 10:1, and the lipid component of the plurality of liposomes consists of a phospholipid and a sterol.

2. The pharmaceutical formulation of claim 1, wherein the free quinolone antibiotic agent is a fluoroquinolone and the quinolone antibiotic agent encapsulated in the plurality of liposomes is a fluoroquinolone.

3. The pharmaceutical formulation of claim 1, wherein the free quinolone antibiotic agent and the quinolone antibiotic agent encapsulated in the plurality of liposomes is independently, ciprofloxacin, enoxacin, gatifloxacin, grepafloxacin, levofloxacin, lomefloxacin, moxifloxacin, nalidixic acid, norfloxacin, ofloxacin, sparfloxacin, trovafloxacin, oxolinic acid, gemifloxacin, or perfloxacin.

4. The pharmaceutical formulation of claim 1, wherein the free quinolone antibiotic agent is ciprofloxacin and the quinolone antibiotic agent encapsulated in the plurality of liposomes is ciprofloxacin.

5. The pharmaceutical formulation of claim 1, wherein the phospholipid is a phosphatidylcholine.

6. The pharmaceutical formulation of claim 5, wherein the phosphatidylcholine is hydrogenated soy phosphatidylcholine (HSPC).

7. The pharmaceutical formulation of claim 5, wherein the sterol is cholesterol.

8. The pharmaceutical formulation of claim 6, wherein the sterol is cholesterol.

9. The pharmaceutical formulation of claim 1, wherein the phospholipid is hydrogenated soy phosphatidylcholine (HSPC), the sterol is cholesterol, the free quinolone antibiotic agent is a fluoroquinolone and the quinolone antibiotic agent encapsulated in the plurality of liposomes is a fluoroquinolone.

10. The pharmaceutical formulation of claim 1, wherein the phospholipid is a phosphatidylcholine, the free quinolone antibiotic agent is ciprofloxacin and the quinolone antibiotic agent encapsulated in the plurality of liposomes is ciprofloxacin.

11. The pharmaceutical formulation of claim 1, wherein the phospholipid is a phosphatidylcholine, the sterol is a cholesterol, the free quinolone antibiotic agent is ciprofloxacin and the quinolone antibiotic agent encapsulated in the plurality of liposomes is ciprofloxacin.

12. The pharmaceutical formulation of claim 1, wherein the phospholipid is a hydrogenated soy phosphatidylcholine (HSPC), the sterol is cholesterol, the free quinolone antibiotic agent is ciprofloxacin and the quinolone antibiotic agent encapsulated in the plurality of liposomes is ciprofloxacin.

13. The pharmaceutical formulation of claim 12, wherein the formulation is an aerosol.

14. The pharmaceutical formulation of claim 1, wherein the ratio by weight of free quinolone antibiotic agent to the encapsulated quinolone antibiotic agent is between about 1:2 and about 2:1.

15. The pharmaceutical formulation of claim 12, wherein the ratio by weight of free ciprofloxacin to the encapsulated ciprofloxacin is between about 1:2 and about 2:1.

16. The pharmaceutical formulation of claim 15, wherein the formulation is an aerosol.

17. A system for treating or providing prophylaxis against a pulmonary infection comprising:
a) the pharmaceutical formulation of claim 1, and
b) an inhalation delivery device.

18. The system of claim 17, wherein the inhalation delivery device is a nebulizer, the phospholipid is hydrogenated soy phosphatidylcholine (HSPC), the sterol is cholesterol, the free quinolone antibiotic agent is ciprofloxacin and the quinolone antibiotic agent encapsulated in the plurality of liposomes is ciprofloxacin.

19. The system of claim 18, wherein the nebulizer is a single dose nebulizer.

20. A method for treating a pulmonary infection in a patient in need thereof comprising, nebulizing the pharmaceutical formulation of claim 1, to generate a nebulized pharmaceutical formulation, administering the nebulized pharmaceutical formulation to the lungs of the patient.

21. A method for treating a pulmonary infection in a patient in need thereof comprising, nebulizing the pharmaceutical formulation of claim 11, to generate a nebulized pharmaceutical formulation, administering the nebulized pharmaceutical formulation to the lungs of the patient.

22. A method for treating a pulmonary infection in a patient in need thereof comprising, nebulizing the pharmaceutical formulation of claim 12, to generate a nebulized pharmaceutical formulation, administering the nebulized pharmaceutical formulation to the lungs of the patient.

23. A method for treating a pulmonary infection in a patient in need thereof comprising, nebulizing the pharmaceutical formulation of claim 15, to generate a nebulized pharmaceutical formulation, administering the nebulized pharmaceutical formulation to the lungs of the patient.

24. The method of claim 20, wherein the patient is a bronchiectasis patient.

25. The method of claim 21, wherein the patient is a bronchiectasis patient.

26. The method of claim 22, wherein the patient is a bronchiectasis patient.

27. The method of claim 23, wherein the patient is a bronchiectasis patient.

28. The method of claim 22, wherein the pulmonary infection is a *Pseudomonas Aeruginosa* infection.

29. The method of claim 23, wherein the pulmonary infection is a *Pseudomonas Aeruginosa* infection.

30. The method of claim 26, wherein the pulmonary infection is a *Pseudomonas Aeruginosa* infection.

* * * * *